United States Patent
Barfield et al.

(10) Patent No.: US 11,612,499 B2
(45) Date of Patent: Mar. 28, 2023

(54) EXPANDABLE INTERBODY IMPLANT

(71) Applicant: Warsaw Orthopedic, Inc., Warsaw, IN (US)

(72) Inventors: Charlie J. Barfield, East Hernando, MS (US); Patrick R. Keene, Henderson, NC (US); Dimitri K. Protopsaltis, Memphis, TN (US); John A. Hall, Germantown, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 17/356,950

(22) Filed: Jun. 24, 2021

(65) Prior Publication Data
US 2022/0409388 A1 Dec. 29, 2022

(51) Int. Cl.
*A61F 2/44* (2006.01)
*A61F 2/30* (2006.01)

(52) U.S. Cl.
CPC .... *A61F 2/447* (2013.01); *A61F 2002/30331* (2013.01); *A61F 2002/30405* (2013.01);
(Continued)

(58) Field of Classification Search
CPC ........ A61F 2/447; A61F 2/442; A61F 2/4455; A61F 2002/30331; A61F 2002/30405;
(Continued)

(56) References Cited

U.S. PATENT DOCUMENTS

| 1,677,337 A | 7/1928 | Grove |
| 3,847,154 A | 11/1974 | Nordin |

(Continued)

FOREIGN PATENT DOCUMENTS

| CN | 107 137 166 A | 9/2017 |
| DE | 44 16 605 C1 | 6/1995 |

(Continued)

OTHER PUBLICATIONS

International Search Report and Written Opinion, PCT/IB2020/000942, dated Aug. 10, 2021.
(Continued)

*Primary Examiner* — Jessica Weiss
(74) *Attorney, Agent, or Firm* — Fox Rothschild LLP

(57) ABSTRACT

An expandable implant having superior and inferior endplates disposed on opposite sides of a core is disclosed. The superior endplate may include a first screw engagement surface disposed on a proximal end thereof and the inferior endplate may include a second screw engagement surface disposed on a proximal end thereof. A pin may extend through corresponding pin apertures of the superior endplate, the inferior endplate, and the core. In various embodiments, the superior endplate and inferior endplate are hingedly connected to the core via the pin. The implant may include a locking screw movable between a locked position and an unlocked position. In the locked position, the locking screw may urge an engagement surface of the superior endplate and inferior endplate such that corresponding interior surfaces of the superior and inferior endplates frictionally engage against a corresponding exterior surface of the core.

20 Claims, 13 Drawing Sheets

(52) U.S. Cl.
CPC ............... *A61F 2002/30428* (2013.01); *A61F 2002/30471* (2013.01); *A61F 2002/30507* (2013.01)

(58) Field of Classification Search
CPC .. A61F 2002/30428; A61F 2002/30471; A61F 2002/30507
USPC ........ 623/17.11–17.16; 606/70–71, 280–299
See application file for complete search history.

(56) References Cited

U.S. PATENT DOCUMENTS

| | | |
|---|---|---|
| 4,401,112 A | 8/1983 | Rezaian |
| 4,553,273 A | 11/1985 | Wu |
| 4,636,217 A | 1/1987 | Ogilvie et al. |
| 4,716,894 A | 1/1988 | Lazzeri et al. |
| 4,759,769 A | 7/1988 | Hedman et al. |
| 5,059,193 A | 10/1991 | Kuslich |
| 5,171,278 A | 12/1992 | Pisharodi |
| 5,228,811 A | 7/1993 | Potter |
| 5,284,483 A | 2/1994 | Johnson et al. |
| 5,336,223 A | 8/1994 | Rogers |
| 5,390,683 A | 2/1995 | Pisharodi |
| 5,522,899 A | 6/1996 | Michelson |
| 5,554,191 A | 9/1996 | Lahille et al. |
| 5,575,790 A | 11/1996 | Chen et al. |
| 5,609,635 A | 3/1997 | Michelson |
| 5,653,762 A | 8/1997 | Pisharodi |
| 5,653,763 A | 8/1997 | Errico et al. |
| 5,658,336 A | 8/1997 | Pisharodi |
| 5,665,122 A | 9/1997 | Kambin |
| 5,693,100 A | 12/1997 | Pisharodi |
| 5,697,977 A | 12/1997 | Pisharodi |
| 5,702,391 A | 12/1997 | Lin |
| 5,702,453 A | 12/1997 | Rabbe et al. |
| 5,702,455 A | 12/1997 | Saggar |
| 5,797,918 A | 8/1998 | McGuire et al. |
| 5,800,550 A | 9/1998 | Sertich |
| 5,865,848 A | 2/1999 | Baker |
| 5,893,890 A | 4/1999 | Pisharodi |
| 5,931,777 A | 8/1999 | Sava |
| 5,941,885 A | 8/1999 | Jackson |
| 5,971,987 A | 10/1999 | Huxel et al. |
| 5,980,522 A | 11/1999 | Koros et al. |
| 6,045,579 A | 4/2000 | Hochshuler et al. |
| 6,074,343 A | 6/2000 | Nathanson et al. |
| 6,080,193 A | 6/2000 | Hochshuler et al. |
| 6,099,531 A | 8/2000 | Bonutti |
| 6,102,949 A | 8/2000 | Biedermann et al. |
| 6,102,950 A | 8/2000 | Vaccaro |
| 6,106,557 A | 8/2000 | Robioneck et al. |
| 6,113,638 A | 9/2000 | Williams et al. |
| 6,117,174 A | 9/2000 | Nolan |
| 6,132,465 A | 10/2000 | Ray et al. |
| 6,159,211 A | 12/2000 | Boriani et al. |
| 6,159,244 A | 12/2000 | Suddaby |
| 6,176,882 B1 | 1/2001 | Biedermann et al. |
| 6,179,873 B1 | 1/2001 | Zientek |
| 6,190,414 B1 | 2/2001 | Young et al. |
| 6,193,757 B1 | 2/2001 | Foley et al. |
| 6,217,579 B1 | 4/2001 | Koros |
| 6,245,108 B1 | 6/2001 | Biscup |
| 6,309,421 B1 | 10/2001 | Pisharodi |
| 6,342,074 B1 | 1/2002 | Simpson |
| 6,371,989 B1 | 4/2002 | Chauvin et al. |
| 6,395,031 B1 | 5/2002 | Foley et al. |
| 6,423,063 B1 | 7/2002 | Bonutti |
| 6,432,106 B1 | 8/2002 | Fraser |
| 6,436,140 B1 | 8/2002 | Liu et al. |
| 6,443,989 B1 | 9/2002 | Jackson |
| 6,443,990 B1 | 9/2002 | Aebi et al. |
| 6,454,806 B1 | 9/2002 | Cohen et al. |
| 6,454,807 B1 | 9/2002 | Jackson |
| 6,461,359 B1 | 10/2002 | Tribus et al. |
| 6,491,724 B1 | 12/2002 | Ferree |
| 6,520,991 B2 | 2/2003 | Huene |
| 6,520,993 B2 | 2/2003 | James et al. |
| 6,524,238 B2 | 2/2003 | Velikaris et al. |
| 6,527,803 B1 | 3/2003 | Crozet et al. |
| 6,562,074 B2 | 5/2003 | Gerbec et al. |
| 6,576,016 B1 | 6/2003 | Hochshuler et al. |
| 6,623,525 B2 | 9/2003 | Ralph et al. |
| 6,629,998 B1 | 10/2003 | Lin |
| 6,635,086 B2 | 10/2003 | Lin |
| 6,648,917 B2 | 11/2003 | Gerbec et al. |
| 6,676,703 B2 | 1/2004 | Biscup |
| 6,685,742 B1 | 2/2004 | Jackson |
| 6,723,126 B1 | 4/2004 | Berry |
| 6,770,096 B2 | 8/2004 | Bolger et al. |
| 6,773,460 B2 | 8/2004 | Jackson |
| 6,821,298 B1 | 11/2004 | Jackson |
| 6,835,206 B2 | 12/2004 | Jackson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,923,814 B1 | 8/2005 | Hildebrand et al. |
| 6,926,737 B2 | 8/2005 | Jackson |
| 6,953,477 B2 | 10/2005 | Berry |
| 6,964,687 B1 | 11/2005 | Bernard et al. |
| 6,974,480 B2 | 12/2005 | Messerli et al. |
| 6,984,234 B2 | 1/2006 | Bray |
| 7,112,222 B2 | 9/2006 | Fraser et al. |
| 7,135,043 B2 | 11/2006 | Nakahara et al. |
| 7,137,997 B2 | 11/2006 | Paul |
| 7,172,627 B2 | 2/2007 | Fiere et al. |
| 7,188,626 B2 | 3/2007 | Foley et al. |
| 7,204,853 B2 | 4/2007 | Gordon et al. |
| 7,232,464 B2 | 6/2007 | Mathieu et al. |
| 7,238,203 B2 | 7/2007 | Bagga et al. |
| 7,255,700 B2 | 8/2007 | Kaiser et al. |
| 7,316,532 B2 | 1/2008 | Matthys-Mark |
| 7,316,714 B2 | 1/2008 | Gordon et al. |
| 7,407,483 B2 | 8/2008 | Perez-Cruet et al. |
| 7,481,766 B2 | 1/2009 | Lee et al. |
| 7,491,168 B2 | 2/2009 | Raymond et al. |
| 7,537,565 B2 | 5/2009 | Bass |
| 7,618,456 B2 | 11/2009 | Mathieu et al. |
| 7,625,394 B2 | 12/2009 | Molz, IV et al. |
| 7,635,366 B2 | 12/2009 | Abdou |
| 7,637,909 B2 | 12/2009 | Lechot et al. |
| 7,655,046 B2 | 2/2010 | Dryer et al. |
| 7,678,148 B2 | 3/2010 | Peterman |
| 7,703,727 B2 | 4/2010 | Selness |
| 7,708,778 B2 | 5/2010 | Gordon et al. |
| 7,708,779 B2 | 5/2010 | Edie et al. |
| 7,727,280 B2 | 6/2010 | McLuen |
| 7,753,958 B2 | 7/2010 | Gordon et al. |
| 7,780,594 B2 | 8/2010 | Hutton |
| 7,806,932 B2 | 10/2010 | Webb et al. |
| 7,815,682 B1 | 10/2010 | Peterson et al. |
| 7,819,801 B2 | 10/2010 | Miles et al. |
| 7,824,428 B2 | 11/2010 | Mikkonen et al. |
| 7,828,849 B2 | 11/2010 | Lim |
| 7,846,167 B2 | 12/2010 | Garcia et al. |
| 7,846,207 B2 | 12/2010 | Lechmann et al. |
| 7,850,731 B2 | 12/2010 | Brittan et al. |
| 7,850,733 B2 | 12/2010 | Baynham et al. |
| 7,862,616 B2 | 1/2011 | Lechmann et al. |
| 7,875,076 B2 | 1/2011 | Mathieu et al. |
| 7,892,173 B2 | 2/2011 | Miles et al. |
| 7,909,869 B2 | 3/2011 | Gordon et al. |
| 7,914,559 B2 | 3/2011 | Carls et al. |
| 7,967,821 B2 | 6/2011 | Sicvol et al. |
| 7,981,031 B2 | 7/2011 | Frasier et al. |
| 8,016,836 B2 | 9/2011 | Corrao et al. |
| 8,062,375 B2 | 11/2011 | Glerum et al. |
| 8,105,382 B2 | 1/2012 | Olmos et al. |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,147,550 B2 | 4/2012 | Gordon et al. |
| 8,172,903 B2 | 5/2012 | Gordon et al. |
| 8,182,539 B2 | 5/2012 | Tyber et al. |
| 8,257,442 B2 | 9/2012 | Edie et al. |

(56) References Cited

U.S. PATENT DOCUMENTS

| | | |
|---|---|---|
| 8,262,570 B2 | 9/2012 | White et al. |
| 8,262,662 B2 | 9/2012 | Beardsley et al. |
| 8,262,710 B2 | 9/2012 | Freedman et al. |
| 8,287,597 B1 | 10/2012 | Pimenta et al. |
| 8,303,498 B2 | 11/2012 | Miles et al. |
| 8,303,658 B2 | 11/2012 | Peterman |
| 8,303,663 B2 | 11/2012 | Jimenez et al. |
| 8,317,866 B2 | 11/2012 | Palmatier et al. |
| 8,323,185 B2 | 12/2012 | Perez-Cruet et al. |
| 8,328,872 B2 | 12/2012 | Duffield et al. |
| 8,343,048 B2 | 1/2013 | Warren, Jr. |
| 8,353,826 B2 | 1/2013 | Weiman |
| 8,355,780 B2 | 1/2013 | Miles et al. |
| 8,382,842 B2 | 2/2013 | Greenhalgh et al. |
| 8,388,527 B2 | 3/2013 | Miles et al. |
| 8,398,713 B2 | 3/2013 | Weiman |
| 8,403,990 B2 | 3/2013 | Dryer et al. |
| 8,419,797 B2 | 4/2013 | Biedermann et al. |
| 8,425,528 B2 | 4/2013 | Berry et al. |
| 8,435,298 B2 | 5/2013 | Weiman |
| 8,480,576 B2 | 7/2013 | Sandhu |
| 8,496,706 B2 | 7/2013 | Ragab et al. |
| 8,500,634 B2 | 8/2013 | Miles et al. |
| 8,506,635 B2 | 8/2013 | Palmatier et al. |
| 8,517,935 B2 | 8/2013 | Marchek et al. |
| 8,518,120 B2 | 8/2013 | Glerum et al. |
| 8,535,380 B2 | 9/2013 | Greenhalgh et al. |
| 8,550,994 B2 | 10/2013 | Miles et al. |
| 8,556,808 B2 | 10/2013 | Miles et al. |
| 8,556,979 B2 | 10/2013 | Glerum et al. |
| 8,579,809 B2 | 11/2013 | Parker |
| 8,579,898 B2 | 11/2013 | Prandi et al. |
| 8,579,979 B2 | 11/2013 | Edie et al. |
| 8,579,981 B2 | 11/2013 | Lim et al. |
| 8,602,984 B2 | 12/2013 | Raymond et al. |
| 8,608,785 B2 | 12/2013 | Reed et al. |
| 8,628,576 B2 | 1/2014 | Triplett et al. |
| 8,628,578 B2 | 1/2014 | Miller et al. |
| 8,632,595 B2 | 1/2014 | Weiman |
| 8,641,768 B2 | 2/2014 | Duffield et al. |
| 8,647,386 B2 | 2/2014 | Gordon et al. |
| 8,663,329 B2 | 3/2014 | Ernst |
| 8,668,419 B2 | 3/2014 | Hardt et al. |
| 8,668,715 B2 | 3/2014 | Sandhu |
| 8,679,183 B2 | 3/2014 | Glerum et al. |
| 8,685,095 B2 | 4/2014 | Miller et al. |
| 8,685,098 B2 | 4/2014 | Glerum et al. |
| 8,696,559 B2 | 4/2014 | Miles et al. |
| 8,709,083 B2 | 4/2014 | Duffield et al. |
| 8,709,085 B2 | 4/2014 | Lechmann et al. |
| 8,709,086 B2 | 4/2014 | Glerum |
| 8,715,285 B2 | 5/2014 | Lewis et al. |
| 8,715,353 B2 | 5/2014 | Bagga et al. |
| 8,740,983 B1 | 6/2014 | Arnold et al. |
| 8,753,271 B1 | 6/2014 | Miles et al. |
| 8,753,396 B1 | 6/2014 | Hockett et al. |
| 8,764,649 B2 | 7/2014 | Miles et al. |
| 8,771,360 B2 | 7/2014 | Jimenez et al. |
| 8,778,025 B2 | 7/2014 | Ragab et al. |
| 8,778,027 B2 | 7/2014 | Medina |
| 8,795,366 B2 | 8/2014 | Varela |
| 8,808,305 B2 | 8/2014 | Kleiner |
| 8,827,902 B2 | 9/2014 | Dietze, Jr. et al. |
| 8,828,085 B1 | 9/2014 | Jensen |
| 8,840,668 B1 | 9/2014 | Donahoe et al. |
| 8,845,731 B2 | 9/2014 | Weiman |
| 8,845,732 B2 | 9/2014 | Weiman |
| 8,845,734 B2 | 9/2014 | Weiman |
| 8,852,252 B2 | 10/2014 | Venturini et al. |
| 8,852,282 B2 | 10/2014 | Farley et al. |
| 8,864,833 B2 | 10/2014 | Glerum et al. |
| 8,882,813 B2 | 11/2014 | Jones et al. |
| 8,888,853 B2 | 11/2014 | Glerum et al. |
| 8,894,708 B2 | 11/2014 | Thalgott et al. |
| 8,894,711 B2 | 11/2014 | Varela |
| 8,894,712 B2 | 11/2014 | Varela |
| 8,906,095 B2 | 12/2014 | Christensen et al. |
| 8,920,500 B1 | 12/2014 | Pimenta et al. |
| 8,926,704 B2 | 1/2015 | Glerum et al. |
| 8,936,641 B2 | 1/2015 | Cain |
| 8,940,049 B1 | 1/2015 | Jimenez et al. |
| 8,968,363 B2 | 3/2015 | Weiman et al. |
| 8,986,344 B2 | 3/2015 | Sandhu |
| 8,992,425 B2 | 3/2015 | Karpowicz et al. |
| 8,992,544 B2 | 3/2015 | Sasing |
| 9,005,292 B2 | 4/2015 | Melamed |
| 9,005,293 B2 | 4/2015 | Moskowitz et al. |
| 9,005,295 B2 | 4/2015 | Kueenzi et al. |
| 9,017,412 B2 | 4/2015 | Wolters et al. |
| 9,034,045 B2 | 5/2015 | Davenport et al. |
| 9,050,146 B2 | 6/2015 | Woolley et al. |
| 9,050,194 B2 | 6/2015 | Thibodeau |
| 9,060,877 B2 | 6/2015 | Kleiner |
| 9,072,548 B2 | 7/2015 | Matityahu |
| 9,072,563 B2 | 7/2015 | Garcia et al. |
| 9,084,591 B2 | 7/2015 | Reglos et al. |
| 9,113,854 B2 | 8/2015 | Ellman |
| 9,119,730 B2 | 9/2015 | Glerum et al. |
| 9,125,757 B2 | 9/2015 | Weiman |
| 9,132,021 B2 | 9/2015 | Mermuys et al. |
| 9,138,217 B2 | 9/2015 | Smith et al. |
| 9,138,330 B2 | 9/2015 | Hansell et al. |
| 9,138,331 B2 | 9/2015 | Aferzon |
| 9,149,367 B2 | 10/2015 | Davenport et al. |
| 9,155,628 B2 | 10/2015 | Glerum et al. |
| 9,155,631 B2 | 10/2015 | Seifert et al. |
| 9,161,841 B2 | 10/2015 | Kana et al. |
| 9,179,903 B2 | 11/2015 | Cianfrani et al. |
| 9,179,952 B2 | 11/2015 | Biedermann et al. |
| 9,186,193 B2 | 11/2015 | Kleiner et al. |
| 9,186,258 B2 | 11/2015 | Davenport et al. |
| 9,192,482 B1 | 11/2015 | Pimenta et al. |
| 9,192,483 B1 | 11/2015 | Radcliffe et al. |
| 9,198,772 B2 | 12/2015 | Weiman |
| 9,204,972 B2 | 12/2015 | Weiman et al. |
| 9,204,974 B2 | 12/2015 | Glerum et al. |
| 9,211,194 B2 | 12/2015 | Bagga et al. |
| 9,211,196 B2 | 12/2015 | Glerum et al. |
| 9,216,095 B2 | 12/2015 | Glerum et al. |
| 9,226,836 B2 | 1/2016 | Glerum |
| 9,233,007 B2 | 1/2016 | Sungarian et al. |
| 9,233,009 B2 | 1/2016 | Gray et al. |
| 9,233,010 B2 | 1/2016 | Thalgott et al. |
| 9,259,327 B2 | 2/2016 | Niemiec et al. |
| 9,271,846 B2 | 3/2016 | Lim et al. |
| 9,308,099 B2 | 4/2016 | Triplett et al. |
| 9,320,610 B2 | 4/2016 | Alheidt et al. |
| 9,351,845 B1 | 5/2016 | Pimenta et al. |
| 9,351,848 B2 | 5/2016 | Glerum et al. |
| 9,357,909 B2 | 6/2016 | Perez-Cruet et al. |
| 9,358,126 B2 | 6/2016 | Glerum et al. |
| 9,358,127 B2 | 6/2016 | Duffield et al. |
| 9,358,128 B2 | 6/2016 | Glerum et al. |
| 9,358,129 B2 | 6/2016 | Weiman |
| 9,364,343 B2 | 6/2016 | Duffield et al. |
| 9,370,434 B2 | 6/2016 | Weiman |
| 9,370,435 B2 | 6/2016 | Walkenhorst et al. |
| 9,381,008 B2 | 7/2016 | Thornburg |
| 9,386,916 B2 | 7/2016 | Predick et al. |
| 9,387,092 B2 | 7/2016 | Mermuys et al. |
| 9,402,673 B2 | 8/2016 | Cormier et al. |
| 9,402,739 B2 | 8/2016 | Weiman et al. |
| 9,408,596 B2 | 8/2016 | Blain |
| 9,408,708 B2 | 8/2016 | Greenhalgh |
| 9,414,828 B2 | 8/2016 | Abidin et al. |
| 9,414,934 B2 | 8/2016 | Cain |
| 9,414,937 B2 | 8/2016 | Carlson et al. |
| 9,421,110 B2 | 8/2016 | Masson et al. |
| 9,427,331 B2 | 8/2016 | Arnin |
| 9,445,919 B2 | 9/2016 | Palmatier et al. |
| 9,452,063 B2 | 9/2016 | Glerum et al. |
| 9,456,903 B2 | 10/2016 | Glerum et al. |
| 9,456,906 B2 | 10/2016 | Gray et al. |
| 9,468,405 B2 | 10/2016 | Miles et al. |

(56) References Cited

U.S. PATENT DOCUMENTS

| | | |
|---|---|---|
| 9,474,622 B2 | 10/2016 | McLaughlin et al. |
| 9,474,625 B2 | 10/2016 | Weiman |
| 9,480,573 B2 | 11/2016 | Perloff et al. |
| 9,480,576 B2 | 11/2016 | Pepper et al. |
| 9,480,579 B2 | 11/2016 | Davenport et al. |
| 9,486,133 B2 | 11/2016 | Lee et al. |
| 9,486,325 B2 | 11/2016 | Davenport et al. |
| 9,486,327 B2 | 11/2016 | Martynova et al. |
| 9,486,328 B2 | 11/2016 | Jimenez et al. |
| 9,492,287 B2 | 11/2016 | Glerum et al. |
| 9,492,288 B2 | 11/2016 | Wagner et al. |
| 9,492,289 B2 | 11/2016 | Davenport et al. |
| 9,498,349 B2 | 11/2016 | Patterson et al. |
| 9,510,954 B2 | 12/2016 | Glerum et al. |
| 9,517,098 B2 | 12/2016 | Anderson |
| 9,522,070 B2 | 12/2016 | Flower et al. |
| 9,526,620 B2 | 12/2016 | Slivka et al. |
| 9,526,625 B2 | 12/2016 | Cain |
| 9,532,821 B2 | 1/2017 | Moskowitz et al. |
| 9,539,103 B2 | 1/2017 | McLaughlin et al. |
| 9,539,108 B2 | 1/2017 | Glerum et al. |
| 9,545,320 B2 | 1/2017 | Padovani et al. |
| 9,549,723 B2 | 1/2017 | Hynes et al. |
| 9,549,824 B2 | 1/2017 | McAfee |
| 9,561,116 B2 | 2/2017 | Weiman et al. |
| 9,566,163 B2 | 2/2017 | Suddaby et al. |
| 9,566,166 B2 | 2/2017 | Parry et al. |
| 9,566,168 B2 | 2/2017 | Glerum et al. |
| 9,572,560 B2 | 2/2017 | Mast et al. |
| 9,572,677 B2 | 2/2017 | Davenport et al. |
| 9,572,681 B2 | 2/2017 | Mathieu et al. |
| 9,579,124 B2 | 2/2017 | Gordon et al. |
| 9,579,139 B2 | 2/2017 | Cormier et al. |
| 9,579,213 B2 | 2/2017 | Bal et al. |
| 9,585,649 B2 | 3/2017 | Blain et al. |
| 9,585,762 B2 | 3/2017 | Suddaby et al. |
| 9,585,766 B2 | 3/2017 | Robinson |
| 9,585,767 B2 | 3/2017 | Robinson |
| 9,592,129 B2 | 3/2017 | Slivka et al. |
| 9,597,195 B2 | 3/2017 | Cain |
| 9,603,643 B2 | 3/2017 | Reed et al. |
| 9,603,713 B2 | 3/2017 | Moskowitz et al. |
| 9,603,717 B2 | 3/2017 | Ibarra et al. |
| 9,615,818 B2 | 4/2017 | Baudouin et al. |
| 9,615,936 B2 | 4/2017 | Duffield et al. |
| 9,622,732 B2 | 4/2017 | Martinelli et al. |
| 9,622,875 B2 | 4/2017 | Moskowitz et al. |
| 9,622,876 B1 | 4/2017 | Greenhalgh et al. |
| 9,629,729 B2 | 4/2017 | Grimberg, Jr. et al. |
| 9,636,097 B2 | 5/2017 | Bass |
| 9,642,720 B2 | 5/2017 | Radcliffe et al. |
| 9,649,198 B2 | 5/2017 | Wolters et al. |
| 9,655,746 B2 | 5/2017 | Seifert |
| 9,655,747 B2 | 5/2017 | Glerum et al. |
| 9,662,224 B2 | 5/2017 | Weiman et al. |
| 9,668,784 B2 | 6/2017 | Brumfield et al. |
| 9,668,876 B2 | 6/2017 | Blain et al. |
| 9,668,879 B2 | 6/2017 | Jimenez et al. |
| 9,675,465 B2 | 6/2017 | Padovani et al. |
| 9,675,467 B2 | 6/2017 | Duffield et al. |
| 9,675,468 B1 | 6/2017 | Jensen |
| 9,693,871 B2 | 7/2017 | Richerme et al. |
| 9,700,428 B2 | 7/2017 | Niemiec et al. |
| 9,707,092 B2 | 7/2017 | Davenport et al. |
| 9,713,536 B2 | 7/2017 | Foley et al. |
| 9,717,601 B2 | 8/2017 | Miller |
| 9,730,684 B2 | 8/2017 | Beale et al. |
| 9,730,806 B2 | 8/2017 | Capote |
| 9,737,288 B2 | 8/2017 | Karpowicz et al. |
| 9,750,617 B2 | 9/2017 | Lim et al. |
| 9,750,618 B1 | 9/2017 | Daffinson et al. |
| 9,757,249 B2 | 9/2017 | Radcliffe et al. |
| 9,763,722 B2 | 9/2017 | Roybal |
| 9,770,343 B2 | 9/2017 | Weiman |
| 9,782,265 B2 | 10/2017 | Weiman et al. |
| 9,788,971 B1 | 10/2017 | Stein |
| 9,795,370 B2 | 10/2017 | O'Connell et al. |
| 9,795,371 B2 | 10/2017 | Miles et al. |
| 9,801,733 B2 | 10/2017 | Wolters et al. |
| 9,801,734 B1 | 10/2017 | Stein et al. |
| 9,808,352 B2 | 11/2017 | Suddaby et al. |
| 9,826,966 B2 | 11/2017 | Mast et al. |
| 9,827,024 B2 | 11/2017 | Cormier et al. |
| 9,827,107 B1 | 11/2017 | Amin |
| 9,833,333 B2 | 12/2017 | Duffield et al. |
| 9,833,336 B2 | 12/2017 | Davenport et al. |
| 9,839,527 B2 | 12/2017 | Robinson |
| 9,839,528 B2 | 12/2017 | Weiman et al. |
| 9,848,993 B2 | 12/2017 | Moskowitz et al. |
| 9,848,996 B2 | 12/2017 | Faulhaber |
| 9,855,151 B2 | 1/2018 | Weiman |
| 9,867,715 B2 | 1/2018 | McLaughlin et al. |
| 9,872,779 B2 | 1/2018 | Miller et al. |
| 9,889,019 B2 | 2/2018 | Rogers et al. |
| 9,907,671 B2 | 3/2018 | Fessler |
| 9,907,673 B2 | 3/2018 | Weiman et al. |
| 9,918,709 B2 | 3/2018 | Sandhu |
| 9,924,859 B2 | 3/2018 | Lee et al. |
| 9,924,940 B2 | 3/2018 | Moskowitz et al. |
| 9,925,062 B2 | 3/2018 | Glerum et al. |
| 9,925,064 B2 | 3/2018 | Duffield et al. |
| 9,931,223 B2 | 4/2018 | Cain |
| 9,937,053 B2 | 4/2018 | Melkent et al. |
| 9,943,342 B2 | 4/2018 | Tanaka et al. |
| 9,943,418 B2 | 4/2018 | Davenport et al. |
| 9,949,775 B2 | 4/2018 | Reed et al. |
| 9,949,841 B2 | 4/2018 | Glerum et al. |
| 9,956,087 B2 | 5/2018 | Seifert et al. |
| 9,962,202 B2 | 5/2018 | Anderson |
| 9,962,270 B2 | 5/2018 | Alheidt et al. |
| 9,962,271 B2 | 5/2018 | Glerum |
| 9,962,272 B1 | 5/2018 | Daffinson et al. |
| 9,968,461 B2 | 5/2018 | Zappacosta et al. |
| 9,968,462 B2 | 5/2018 | Weiman |
| 9,974,531 B2 | 5/2018 | Miles et al. |
| 9,974,662 B2 | 5/2018 | Hessler et al. |
| 9,974,664 B2 | 5/2018 | Emerick et al. |
| 9,980,825 B2 | 5/2018 | Nichols et al. |
| 9,980,826 B2 | 5/2018 | Martynova et al. |
| 9,987,141 B2 | 6/2018 | Duffield et al. |
| 9,987,143 B2 | 6/2018 | Robinson et al. |
| 9,987,144 B2 | 6/2018 | Seifert et al. |
| 9,987,146 B1 | 6/2018 | Lentner et al. |
| 9,993,239 B2 | 6/2018 | Karpowicz et al. |
| 9,993,350 B2 | 6/2018 | Cain |
| 10,004,607 B2 | 6/2018 | Weiman et al. |
| 10,016,282 B2 | 7/2018 | Seifert et al. |
| 10,016,284 B2 | 7/2018 | Moskowitz et al. |
| 10,022,239 B1 | 7/2018 | Lentner et al. |
| 10,028,842 B2 | 7/2018 | Gray et al. |
| 10,034,765 B2 | 7/2018 | Blain et al. |
| 10,034,769 B2 | 7/2018 | Baynham |
| 10,034,771 B2 | 7/2018 | Capote et al. |
| 10,034,772 B2 | 7/2018 | Glerum et al. |
| 10,034,773 B2 | 7/2018 | McLaughlin et al. |
| 10,039,539 B2 | 8/2018 | Friedrich et al. |
| 10,039,650 B2 | 8/2018 | Lamborne et al. |
| 10,052,214 B2 | 8/2018 | Jimenez et al. |
| 10,058,431 B2 | 8/2018 | Tyber et al. |
| 10,060,469 B2 | 8/2018 | Jimenez et al. |
| 10,070,852 B2 | 9/2018 | Mast et al. |
| 10,076,320 B2 | 9/2018 | Mast et al. |
| 10,076,423 B2 | 9/2018 | Miller et al. |
| 10,080,666 B2 | 9/2018 | Suddaby et al. |
| 10,080,669 B2 | 9/2018 | Davenport et al. |
| 10,085,846 B2 | 10/2018 | Grotz |
| 10,085,849 B2 | 10/2018 | Weiman et al. |
| 10,092,417 B2 | 10/2018 | Weiman et al. |
| 10,098,758 B2 | 10/2018 | Matthews et al. |
| 10,098,759 B2 | 10/2018 | Weiman |
| 10,111,755 B2 | 10/2018 | Foley et al. |
| 10,111,758 B2 | 10/2018 | Robinson |
| 10,117,754 B2 | 11/2018 | Davenport et al. |
| 10,117,755 B2 | 11/2018 | Emerick et al. |

(56) References Cited

U.S. PATENT DOCUMENTS

| | | |
|---|---|---|
| 10,137,002 B2 | 11/2018 | Padovani et al. |
| 10,137,006 B2 | 11/2018 | Dewey et al. |
| 10,137,007 B2 | 11/2018 | Dewey et al. |
| 10,137,009 B2 | 11/2018 | Weiman et al. |
| 10,149,671 B2 | 12/2018 | Predick et al. |
| 10,149,710 B2 | 12/2018 | Tanaka et al. |
| 10,154,781 B2 | 12/2018 | Weiman |
| 10,154,912 B2 | 12/2018 | Glerum |
| 10,154,914 B2 | 12/2018 | Robinson |
| 10,159,584 B2 | 12/2018 | Carnes et al. |
| 10,166,117 B1 | 1/2019 | Daffinson et al. |
| 10,172,515 B2 | 1/2019 | Lee et al. |
| 10,172,652 B2 | 1/2019 | Woolley et al. |
| 10,178,987 B2 | 1/2019 | Predick et al. |
| 10,179,053 B2 | 1/2019 | Zappacosta et al. |
| 10,182,922 B2 | 1/2019 | Nichols et al. |
| 10,188,527 B2 | 1/2019 | Rogers et al. |
| 10,195,050 B2 | 2/2019 | Palmatier et al. |
| 10,201,431 B2 | 2/2019 | Slater et al. |
| 10,213,192 B2 | 2/2019 | Capote |
| 10,213,193 B2 | 2/2019 | Karpowicz et al. |
| 10,219,798 B2 | 3/2019 | Capote |
| 10,219,913 B2 | 3/2019 | Matthews et al. |
| 10,219,914 B2 | 3/2019 | Faulhaber |
| 10,219,915 B1 | 3/2019 | Stein |
| 10,226,356 B2 | 3/2019 | Grotz |
| 10,226,359 B2 | 3/2019 | Glerum et al. |
| 10,238,375 B2 | 3/2019 | O'Connell et al. |
| 10,238,383 B2 | 3/2019 | Moskowitz et al. |
| 10,238,503 B2 | 3/2019 | Branch et al. |
| 10,245,015 B2 | 4/2019 | Predick et al. |
| 10,251,643 B2 | 4/2019 | Moskowitz et al. |
| 10,265,191 B2 | 4/2019 | Lim et al. |
| 10,278,686 B2 | 5/2019 | Baudouin et al. |
| 10,278,786 B2 | 5/2019 | Friedrich et al. |
| 10,278,830 B1 | 5/2019 | Walker et al. |
| 10,278,831 B2 | 5/2019 | Sandul |
| 10,278,832 B2 | 5/2019 | Nichols et al. |
| 10,285,680 B2 | 5/2019 | Friedrich et al. |
| 10,285,819 B2 | 5/2019 | Greenhalgh |
| 10,285,824 B2 | 5/2019 | Robinson |
| 10,292,828 B2 | 5/2019 | Greenhalgh |
| 10,299,777 B2 | 5/2019 | Mast et al. |
| 10,299,934 B2 | 5/2019 | Seifert et al. |
| 10,299,937 B2 | 5/2019 | McAfee |
| 10,307,268 B2 | 6/2019 | Moskowitz et al. |
| 10,314,622 B2 | 6/2019 | Brumfield et al. |
| 10,314,719 B2 | 6/2019 | Hessler et al. |
| 10,322,007 B2 | 6/2019 | Masson et al. |
| 10,322,009 B2 | 6/2019 | Aghayev et al. |
| 10,327,909 B2 | 6/2019 | Baynham |
| 10,327,912 B1 | 6/2019 | Suddaby |
| 10,327,917 B2 | 6/2019 | Glerum et al. |
| 10,342,675 B2 | 7/2019 | Alheidt |
| 10,350,085 B2 | 7/2019 | Glerum et al. |
| 10,357,233 B2 | 7/2019 | Miles et al. |
| 10,363,142 B2 | 7/2019 | McClintock et al. |
| 10,363,144 B2 | 7/2019 | Overes et al. |
| 10,369,004 B2 | 8/2019 | Faulhaber |
| 10,369,008 B2 | 8/2019 | Jimenez et al. |
| 10,369,010 B2 | 8/2019 | Robinson et al. |
| 10,369,012 B2 | 8/2019 | Fessler |
| 10,376,377 B2 | 8/2019 | Seifert et al. |
| 10,390,962 B2 | 8/2019 | Weiman |
| 10,390,964 B2 | 8/2019 | Faulhaber |
| 10,398,563 B2 | 9/2019 | Engstrom |
| 10,398,566 B2 | 9/2019 | Olmos et al. |
| 10,413,419 B2 | 9/2019 | Thibodeau |
| 10,413,422 B2 | 9/2019 | Flower et al. |
| 10,413,423 B2 | 9/2019 | Overes et al. |
| 10,426,450 B2 | 10/2019 | Vogel et al. |
| 10,426,633 B2 | 10/2019 | Moskowitz et al. |
| 10,426,634 B1 | 10/2019 | Al-Jazaeri et al. |
| 10,441,430 B2 | 10/2019 | Ludwig et al. |
| 10,449,056 B2 | 10/2019 | Cain |
| 10,456,122 B2 | 10/2019 | Koltz et al. |
| 10,470,894 B2 | 11/2019 | Foley et al. |
| 10,478,319 B2 | 11/2019 | Moskowitz et al. |
| 10,492,912 B2 | 12/2019 | Gregersen et al. |
| 10,492,922 B2 | 12/2019 | Mathieu et al. |
| 10,492,924 B2 | 12/2019 | Stein et al. |
| 10,500,064 B2 | 12/2019 | Robinson |
| 10,512,550 B2 | 12/2019 | Bechtel et al. |
| 10,517,645 B2 | 12/2019 | van der Pol |
| 10,524,924 B2 | 1/2020 | Davenport et al. |
| 10,531,903 B2 | 1/2020 | Daly et al. |
| 10,537,436 B2 | 1/2020 | Maguire et al. |
| 10,537,438 B2 | 1/2020 | Martynova et al. |
| 10,555,729 B1 | 2/2020 | Cole et al. |
| 10,561,411 B1 | 2/2020 | Cole et al. |
| 10,575,889 B2 | 3/2020 | Roybal |
| 10,575,960 B2 | 3/2020 | Duffield et al. |
| 10,582,959 B2 | 3/2020 | Langer et al. |
| 10,583,015 B2 | 3/2020 | Olmos et al. |
| 10,603,078 B2 | 3/2020 | Simpson et al. |
| 10,610,376 B2 | 4/2020 | Kuyler et al. |
| 10,624,757 B2 | 4/2020 | Bost et al. |
| 10,624,758 B2 | 4/2020 | Slivka et al. |
| 10,624,761 B2 | 4/2020 | Davenport et al. |
| 10,639,163 B2 | 5/2020 | Tyber et al. |
| 10,639,166 B2 | 5/2020 | Weiman et al. |
| 10,653,458 B2 | 5/2020 | Tanaka et al. |
| 10,667,925 B2 | 6/2020 | Emerick et al. |
| 10,667,927 B2 | 6/2020 | Lamborne et al. |
| 10,675,157 B2 | 6/2020 | Zakelj et al. |
| 10,682,241 B2 | 6/2020 | Glerum et al. |
| 10,687,963 B2 | 6/2020 | Jimenez et al. |
| 10,702,393 B2 | 7/2020 | Davenport et al. |
| 10,709,569 B2 | 7/2020 | McLaughlin et al. |
| 10,709,571 B2 | 7/2020 | Iott et al. |
| 10,709,572 B2 | 7/2020 | Daffinson et al. |
| 10,709,575 B2 | 7/2020 | Robinson |
| 10,722,377 B2 | 7/2020 | Glerum et al. |
| 10,722,379 B2 | 7/2020 | McLaughlin et al. |
| 10,729,561 B2 | 8/2020 | Glerum |
| 10,743,858 B1 | 8/2020 | Cole et al. |
| 10,744,002 B2 | 8/2020 | Glerum et al. |
| 10,758,366 B2 | 9/2020 | Daffinson et al. |
| 10,758,367 B2 | 9/2020 | Weiman et al. |
| 10,758,369 B2 | 9/2020 | Rogers et al. |
| 10,765,528 B2 | 9/2020 | Weiman et al. |
| 10,772,737 B2 | 9/2020 | Gray et al. |
| 10,779,955 B2 | 9/2020 | Kuyler et al. |
| 10,779,957 B2 | 9/2020 | Weiman et al. |
| 10,786,364 B2 | 9/2020 | Davenport et al. |
| 10,786,369 B2 | 9/2020 | Carnes et al. |
| 10,799,368 B2 | 10/2020 | Glerum et al. |
| 10,835,387 B2 | 11/2020 | Weiman et al. |
| 10,842,640 B2 | 11/2020 | Weiman et al. |
| 10,842,644 B2 | 11/2020 | Weiman et al. |
| 10,856,997 B2 | 12/2020 | Cowan et al. |
| 10,869,769 B2 | 12/2020 | Eisen et al. |
| 10,874,447 B2 | 12/2020 | Tanaka et al. |
| 10,874,522 B2 | 12/2020 | Weiman |
| 10,874,523 B2 | 12/2020 | Weiman et al. |
| 10,874,524 B2 | 12/2020 | Bjork |
| 10,881,524 B2 | 1/2021 | Eisen et al. |
| 10,881,531 B2 | 1/2021 | Berry |
| 10,888,431 B1 | 1/2021 | Robinson |
| 10,898,344 B2 | 1/2021 | Alheidt et al. |
| 10,898,346 B1 | 1/2021 | Suddaby |
| 10,925,656 B2 | 2/2021 | Cole et al. |
| 10,925,750 B2 | 2/2021 | Zappacosta et al. |
| 10,925,752 B2 | 2/2021 | Weiman |
| 10,932,920 B2 | 3/2021 | Dewey et al. |
| 10,940,014 B2 | 3/2021 | Greenhalgh |
| 10,945,858 B2 | 3/2021 | Bechtel et al. |
| 10,952,866 B2 | 3/2021 | Warren et al. |
| 10,959,855 B2 | 3/2021 | Miller et al. |
| 10,959,856 B2 | 3/2021 | Seifert et al. |
| 10,973,649 B2 | 4/2021 | Weiman et al. |
| 10,973,650 B2 | 4/2021 | Stein |
| 10,980,642 B2 | 4/2021 | Glerum et al. |
| 10,980,644 B2 | 4/2021 | Purcell et al. |

(56) References Cited

U.S. PATENT DOCUMENTS

| | | | |
|---|---|---|---|
| 10,993,814 B2 | 5/2021 | Wolters | |
| 11,007,067 B2 | 5/2021 | Masson et al. | |
| 11,013,617 B2 | 5/2021 | Weiman et al. | |
| 11,020,238 B2 | 6/2021 | Nichols et al. | |
| 11,020,239 B2 | 6/2021 | Miller et al. | |
| 11,026,804 B2 | 6/2021 | Jimenez et al. | |
| 11,026,812 B2 | 6/2021 | Daffinson et al. | |
| 11,033,401 B2 | 6/2021 | Shoshtaev | |
| 11,033,402 B2 | 6/2021 | Melkent et al. | |
| 11,033,404 B2 | 6/2021 | Faulhaber | |
| 11,039,935 B2 | 6/2021 | McAfee | |
| 11,045,326 B2 | 6/2021 | Seifert et al. | |
| 11,045,327 B2 | 6/2021 | Nichols et al. | |
| 11,051,949 B2 | 7/2021 | Walker et al. | |
| 11,051,951 B2 | 7/2021 | Robinson et al. | |
| 11,058,469 B2 | 7/2021 | Mahajan et al. | |
| 11,065,127 B1 | 7/2021 | Lentner et al. | |
| 11,065,129 B2 | 7/2021 | Sandul | |
| 11,065,130 B2 | 7/2021 | Branch et al. | |
| 11,076,966 B2 | 8/2021 | Faulhaber | |
| 11,083,584 B2 | 8/2021 | Lauf et al. | |
| 11,083,595 B2 | 8/2021 | Robinson | |
| 11,090,167 B2 | 8/2021 | Emerick et al. | |
| 11,096,795 B2 | 8/2021 | Padovani et al. | |
| 11,096,797 B2 | 8/2021 | Moskowitz et al. | |
| 11,103,366 B2 | 8/2021 | Glerum et al. | |
| RE48,719 E | 9/2021 | Suddaby et al. | |
| 11,109,980 B2 | 9/2021 | Seifert et al. | |
| 11,116,644 B2 | 9/2021 | Marrocco et al. | |
| 11,123,198 B2 | 9/2021 | Black et al. | |
| 11,123,200 B2 | 9/2021 | Faulhaber | |
| 11,129,731 B2 | 9/2021 | Miller et al. | |
| 11,135,071 B2 | 10/2021 | Dewey et al. | |
| 11,147,680 B2 | 10/2021 | Tyber et al. | |
| 11,154,404 B2 | 10/2021 | Freedman et al. | |
| 11,160,666 B2 | 11/2021 | Burkhardt et al. | |
| 11,160,669 B2 | 11/2021 | Rogers et al. | |
| 11,166,826 B2 | 11/2021 | Huang | |
| 11,173,044 B1 | 11/2021 | Jones et al. | |
| 11,179,234 B2 | 11/2021 | Dacosta et al. | |
| 11,285,014 B2 | 3/2022 | Josse et al. | |
| 11,376,134 B1 | 7/2022 | Dewey et al. | |
| 2002/0045943 A1 | 4/2002 | Uk | |
| 2002/0045945 A1 | 4/2002 | Liu et al. | |
| 2002/0055741 A1 | 5/2002 | Schlapfer et al. | |
| 2002/0116066 A1 | 8/2002 | Chauvin et al. | |
| 2002/0128713 A1 | 9/2002 | Ferree | |
| 2002/0151976 A1 | 10/2002 | Foley et al. | |
| 2002/0183762 A1 | 12/2002 | Anderson et al. | |
| 2003/0050701 A1 | 3/2003 | Michelson | |
| 2003/0130739 A1 | 7/2003 | Gerbec et al. | |
| 2003/0163132 A1 | 8/2003 | Chin | |
| 2004/0102778 A1 | 5/2004 | Huebner et al. | |
| 2004/0172134 A1 | 9/2004 | Berry | |
| 2004/0186570 A1 | 9/2004 | Rapp | |
| 2004/0193158 A1 | 9/2004 | Lim et al. | |
| 2004/0204713 A1 | 10/2004 | Abdou | |
| 2004/0249461 A1 | 12/2004 | Ferree | |
| 2004/0254643 A1 | 12/2004 | Jackson | |
| 2004/0254644 A1 | 12/2004 | Taylor | |
| 2005/0015149 A1 | 1/2005 | Michelson | |
| 2005/0033429 A1 | 2/2005 | Kuo | |
| 2005/0033439 A1 | 2/2005 | Gordon et al. | |
| 2005/0228398 A1 | 10/2005 | Rathbun et al. | |
| 2006/0122701 A1 | 6/2006 | Kiester | |
| 2006/0129244 A1 | 6/2006 | Ensign | |
| 2006/0260446 A1 | 11/2006 | Chang | |
| 2007/0173840 A1 | 7/2007 | Huebner | |
| 2007/0218750 A1 | 9/2007 | Corrao et al. | |
| 2007/0233150 A1 | 10/2007 | Blain et al. | |
| 2007/0270859 A1 | 11/2007 | Companioni et al. | |
| 2008/0058804 A1 | 3/2008 | Lechot et al. | |
| 2008/0132959 A1 | 6/2008 | Mikkonen et al. | |
| 2008/0140207 A1 | 6/2008 | Olmos et al. | |
| 2009/0024158 A1 | 1/2009 | Viker | |
| 2009/0292361 A1 | 11/2009 | Lopez | |
| 2010/0076440 A1 | 3/2010 | Pamichev et al. | |
| 2010/0082109 A1 | 4/2010 | Greenhalgh et al. | |
| 2010/0152853 A1 | 6/2010 | Kirschman | |
| 2010/0191336 A1 | 7/2010 | Greenhalgh | |
| 2010/0211176 A1 | 8/2010 | Greenhalgh | |
| 2010/0286777 A1 | 11/2010 | Errico et al. | |
| 2011/0118843 A1 | 5/2011 | Mathieu et al. | |
| 2011/0130838 A1 | 6/2011 | Morgenstern Lopez | |
| 2011/0153020 A1 | 6/2011 | Abdelgany et al. | |
| 2011/0218572 A1 | 9/2011 | Lechmann et al. | |
| 2012/0004732 A1* | 1/2012 | Goel | A61F 2/447 623/17.16 |
| 2012/0095515 A1 | 4/2012 | Hamilton | |
| 2012/0101581 A1 | 4/2012 | Mathieu et al. | |
| 2012/0109142 A1 | 5/2012 | Dayan | |
| 2012/0109309 A1 | 5/2012 | Mathieu et al. | |
| 2012/0109310 A1 | 5/2012 | Mathieu et al. | |
| 2012/0109312 A1 | 5/2012 | Mathieu et al. | |
| 2012/0109313 A1 | 5/2012 | Mathieu et al. | |
| 2012/0123546 A1 | 5/2012 | Medina | |
| 2012/0143195 A1 | 6/2012 | Sander | |
| 2012/0150237 A1 | 6/2012 | Combrowski | |
| 2012/0197401 A1 | 8/2012 | Duncan et al. | |
| 2012/0209385 A1 | 8/2012 | Aferzon | |
| 2012/0215313 A1* | 8/2012 | Saidha | A61F 2/4455 623/17.16 |
| 2012/0215316 A1 | 8/2012 | Mohr et al. | |
| 2013/0158664 A1* | 6/2013 | Palmatier | A61F 2/4425 623/17.16 |
| 2013/0184823 A1* | 7/2013 | Malberg | A61F 2/442 623/17.13 |
| 2013/0190876 A1 | 7/2013 | Drochner et al. | |
| 2013/0211526 A1 | 8/2013 | Alheidt et al. | |
| 2013/0226191 A1 | 8/2013 | Thoren et al. | |
| 2013/0231747 A1 | 9/2013 | Olmos et al. | |
| 2013/0304136 A1 | 11/2013 | Gourlaouen-Preissler et al. | |
| 2013/0317312 A1 | 11/2013 | Eastlack et al. | |
| 2014/0018816 A1 | 1/2014 | Fenn et al. | |
| 2014/0107790 A1 | 4/2014 | Combrowski | |
| 2014/0114321 A1 | 4/2014 | Davenport et al. | |
| 2014/0114420 A1 | 4/2014 | Robinson | |
| 2014/0148904 A1* | 5/2014 | Robinson | A61F 2/447 623/17.16 |
| 2014/0163682 A1 | 6/2014 | Iott et al. | |
| 2014/0180419 A1 | 6/2014 | Dmuschewsky | |
| 2014/0194992 A1 | 7/2014 | Medina | |
| 2014/0249631 A1 | 9/2014 | Weiman | |
| 2014/0277471 A1 | 9/2014 | Gray et al. | |
| 2014/0277487 A1 | 9/2014 | Davenport et al. | |
| 2014/0277500 A1 | 9/2014 | Logan et al. | |
| 2014/0303674 A1 | 10/2014 | Basing | |
| 2014/0364855 A1 | 12/2014 | Stoll et al. | |
| 2015/0223945 A1 | 8/2015 | Weiman et al. | |
| 2015/0230931 A1 | 8/2015 | Greenhalgh | |
| 2015/0238236 A1 | 8/2015 | Basing | |
| 2015/0354635 A1 | 12/2015 | McClymont et al. | |
| 2016/0008924 A1 | 1/2016 | Canourgues et al. | |
| 2016/0022434 A1 | 1/2016 | Robinson | |
| 2016/0058571 A1 | 3/2016 | McLaughlin et al. | |
| 2016/0081681 A1 | 3/2016 | Waugh et al. | |
| 2016/0089247 A1 | 3/2016 | Nichols et al. | |
| 2016/0095710 A1 | 4/2016 | Juszczyk et al. | |
| 2016/0095718 A1 | 4/2016 | Burkhardt et al. | |
| 2016/0199073 A1 | 7/2016 | Nino et al. | |
| 2016/0242930 A1 | 8/2016 | Duffield et al. | |
| 2016/0256291 A1 | 9/2016 | Miller | |
| 2016/0278830 A1 | 9/2016 | Arrington | |
| 2016/0296340 A1 | 10/2016 | Gordon et al. | |
| 2016/0310291 A1 | 10/2016 | Greenhalgh | |
| 2016/0345952 A1 | 12/2016 | Kucharzyk et al. | |
| 2016/0367377 A1 | 12/2016 | Faulhaber | |
| 2017/0010025 A1 | 1/2017 | Mayershofer | |
| 2017/0029635 A1 | 2/2017 | Doll et al. | |
| 2017/0035406 A1 | 2/2017 | Abidin et al. | |
| 2017/0049651 A1 | 2/2017 | Lim et al. | |
| 2017/0049653 A1 | 2/2017 | Lim et al. | |
| 2017/0095345 A1 | 4/2017 | Davenport et al. | |
| 2017/0100255 A1 | 4/2017 | Hleihil et al. | |

(56) References Cited

U.S. PATENT DOCUMENTS

| | | |
|---|---|---|
| 2017/0100257 A1 | 4/2017 | Weiman et al. |
| 2017/0105844 A1 | 4/2017 | Kuyler et al. |
| 2017/0112630 A1 | 4/2017 | Kuyler et al. |
| 2017/0151065 A1 | 6/2017 | Warren et al. |
| 2017/0156882 A1 | 6/2017 | Rathbun et al. |
| 2017/0156884 A1 | 6/2017 | Rathbun et al. |
| 2017/0189204 A1 | 7/2017 | Riemhofer et al. |
| 2017/0202678 A1 | 7/2017 | Duffield et al. |
| 2017/0215856 A1 | 8/2017 | Martinelli et al. |
| 2017/0224502 A1 | 8/2017 | Wolters et al. |
| 2017/0224504 A1 | 8/2017 | Butler et al. |
| 2017/0231675 A1 | 8/2017 | Combrowski |
| 2017/0246006 A1 | 8/2017 | Carnes et al. |
| 2017/0290677 A1 | 10/2017 | Olmos et al. |
| 2017/0296352 A1 | 10/2017 | Richerme et al. |
| 2017/0367842 A1 | 12/2017 | Predick et al. |
| 2017/0367843 A1 | 12/2017 | Eisen et al. |
| 2017/0367844 A1 | 12/2017 | Eisen et al. |
| 2017/0367845 A1 | 12/2017 | Eisen et al. |
| 2018/0000606 A1 | 1/2018 | Hessler et al. |
| 2018/0030362 A1 | 2/2018 | Kosler et al. |
| 2018/0031810 A1 | 2/2018 | Hsu et al. |
| 2018/0036136 A1 | 2/2018 | Duffield et al. |
| 2018/0036138 A1 | 2/2018 | Robinson |
| 2018/0104066 A1 | 4/2018 | Bae et al. |
| 2018/0116891 A1 | 5/2018 | Beale et al. |
| 2018/0193160 A1 | 7/2018 | Hsu et al. |
| 2018/0193164 A1 | 7/2018 | Shoshtaev |
| 2018/0206999 A1 | 7/2018 | Suddaby |
| 2018/0256356 A1 | 9/2018 | Robinson et al. |
| 2018/0256359 A1 | 9/2018 | Greenhalgh |
| 2018/0256360 A1 | 9/2018 | Cain |
| 2018/0256362 A1 | 9/2018 | Slivka et al. |
| 2018/0263784 A1 | 9/2018 | Bechtel et al. |
| 2018/0280142 A1 | 10/2018 | Schultz et al. |
| 2018/0303473 A1 | 10/2018 | Spann et al. |
| 2018/0303621 A1 | 10/2018 | Brotman et al. |
| 2018/0303625 A1 | 10/2018 | Alheidt et al. |
| 2018/0311048 A1 | 11/2018 | Glerum et al. |
| 2018/0318101 A1 | 11/2018 | Engstrom |
| 2018/0318102 A1 | 11/2018 | Seifert et al. |
| 2018/0325574 A1 | 11/2018 | Bjork et al. |
| 2018/0338838 A1 | 11/2018 | Cryder et al. |
| 2018/0338841 A1 | 11/2018 | Miller et al. |
| 2018/0344307 A1 | 12/2018 | Hynes et al. |
| 2018/0360616 A1 | 12/2018 | Luu |
| 2019/0000640 A1 | 1/2019 | Weiman |
| 2019/0000702 A1 | 1/2019 | Lim et al. |
| 2019/0000707 A1 | 1/2019 | Lim et al. |
| 2019/0020121 A1 | 1/2019 | Paulotto et al. |
| 2019/0021716 A1 | 1/2019 | Waugh et al. |
| 2019/0021873 A1 | 1/2019 | Dmuschewsky |
| 2019/0046329 A1 | 2/2019 | Padovani et al. |
| 2019/0046381 A1 | 2/2019 | Lim et al. |
| 2019/0046383 A1 | 2/2019 | Lim et al. |
| 2019/0060083 A1 | 2/2019 | Weiman et al. |
| 2019/0082949 A1 | 3/2019 | Weiman |
| 2019/0083081 A1 | 3/2019 | Ortiz et al. |
| 2019/0091033 A1 | 3/2019 | Dewey et al. |
| 2019/0105175 A1 | 4/2019 | Zappacosta et al. |
| 2019/0125328 A1 | 5/2019 | Blain |
| 2019/0133434 A1 | 5/2019 | Lee et al. |
| 2019/0133645 A1 | 5/2019 | Gordon et al. |
| 2019/0133779 A1 | 5/2019 | McLaughlin et al. |
| 2019/0133780 A1 | 5/2019 | Matthews et al. |
| 2019/0133784 A1 | 5/2019 | Gunn et al. |
| 2019/0133788 A1 | 5/2019 | Weiman et al. |
| 2019/0142480 A1 | 5/2019 | Woolley et al. |
| 2019/0151115 A1 | 5/2019 | Nichols et al. |
| 2019/0183656 A1 | 6/2019 | Stein |
| 2019/0201209 A1 | 7/2019 | Branch et al. |
| 2019/0201210 A1 | 7/2019 | Besaw et al. |
| 2019/0209155 A1 | 7/2019 | Mast et al. |
| 2019/0216453 A1 | 7/2019 | Predick et al. |
| 2019/0231552 A1 | 8/2019 | Sandul |
| 2019/0240039 A1 | 8/2019 | Walker et al. |
| 2019/0240043 A1 | 8/2019 | Greenhalgh |
| 2019/0247098 A1 | 8/2019 | Brumfield et al. |
| 2019/0254650 A1 | 8/2019 | Martinelli et al. |
| 2019/0254838 A1 | 8/2019 | Miller et al. |
| 2019/0254839 A1 | 8/2019 | Nichols et al. |
| 2019/0262009 A1 | 8/2019 | Cheng |
| 2019/0262139 A1 | 8/2019 | Wolters |
| 2019/0269521 A1 | 9/2019 | Shoshtaev |
| 2019/0274670 A1 | 9/2019 | O'Connell et al. |
| 2019/0274671 A1 | 9/2019 | Lauf et al. |
| 2019/0274836 A1 | 9/2019 | Eisen et al. |
| 2019/0282373 A1 | 9/2019 | Alheidt |
| 2019/0290446 A1 | 9/2019 | Masson et al. |
| 2019/0290447 A1 | 9/2019 | Stein |
| 2019/0298416 A1 | 10/2019 | Rezach |
| 2019/0298524 A1 | 10/2019 | Lauf et al. |
| 2019/0298540 A1 | 10/2019 | Aghayev et al. |
| 2019/0321022 A1 | 10/2019 | Karpowicz et al. |
| 2019/0321190 A1 | 10/2019 | Wagner et al. |
| 2019/0328539 A1 | 10/2019 | Suh et al. |
| 2019/0328540 A1 | 10/2019 | Seifert et al. |
| 2019/0329388 A1 | 10/2019 | Erickson et al. |
| 2019/0336301 A1 | 11/2019 | Engstrom |
| 2019/0336304 A1 | 11/2019 | Burkhardt et al. |
| 2019/0350573 A1 | 11/2019 | Vogel et al. |
| 2019/0358049 A1 | 11/2019 | Faulhaber |
| 2019/0358050 A1 | 11/2019 | Fessler |
| 2019/0358051 A1 | 11/2019 | Flower et al. |
| 2019/0380840 A1 | 12/2019 | Tyber et al. |
| 2019/0388232 A1 | 12/2019 | Purcell et al. |
| 2020/0008951 A1 | 1/2020 | McClintock et al. |
| 2020/0030114 A1 | 1/2020 | Cain |
| 2020/0030116 A1 | 1/2020 | Jimenez et al. |
| 2020/0038200 A1 | 2/2020 | Foley et al. |
| 2020/0054461 A1 | 2/2020 | Marrocco et al. |
| 2020/0060844 A1 | 2/2020 | Mathieu et al. |
| 2020/0069316 A1 | 3/2020 | DeSoutter et al. |
| 2020/0078190 A1 | 3/2020 | Rogers et al. |
| 2020/0093526 A1 | 3/2020 | Daly et al. |
| 2020/0093607 A1 | 3/2020 | Davenport et al. |
| 2020/0093609 A1 | 3/2020 | Shoshtaev |
| 2020/0100904 A1 | 4/2020 | Stein et al. |
| 2020/0129306 A1 | 4/2020 | Miller et al. |
| 2020/0129307 A1 | 4/2020 | Hunziker et al. |
| 2020/0138591 A1 | 5/2020 | Moskowitz et al. |
| 2020/0138593 A1 | 5/2020 | Martynova et al. |
| 2020/0146840 A1 | 5/2020 | Black et al. |
| 2020/0179120 A1 | 6/2020 | Bielenstein et al. |
| 2020/0205993 A1 | 7/2020 | Davenport et al. |
| 2020/0214754 A1 | 7/2020 | Bowen et al. |
| 2020/0222202 A1 | 7/2020 | Kuyler et al. |
| 2020/0229944 A1 | 7/2020 | Suh et al. |
| 2020/0246159 A1 | 8/2020 | Suh et al. |
| 2020/0246162 A1 | 8/2020 | Schultz et al. |
| 2020/0261242 A1 | 8/2020 | Bost et al. |
| 2020/0268524 A1 | 8/2020 | Glerum et al. |
| 2020/0276028 A1 | 9/2020 | Blain et al. |
| 2020/0281741 A1 | 9/2020 | Grotz |
| 2020/0289287 A1 | 9/2020 | Emerick et al. |
| 2020/0297507 A1 | 9/2020 | Iott et al. |
| 2020/0330239 A1 | 10/2020 | Davenport et al. |
| 2020/0330245 A1 | 10/2020 | Glerum |
| 2020/0345511 A1 | 11/2020 | Daffinson et al. |
| 2020/0352731 A1 | 11/2020 | Berry |
| 2020/0352738 A1 | 11/2020 | Berry |
| 2020/0360153 A1 | 11/2020 | Weiman et al. |
| 2020/0375753 A1 | 12/2020 | McLaughlin et al. |
| 2020/0375755 A1 | 12/2020 | Cain |
| 2020/0383797 A1 | 12/2020 | Predick et al. |
| 2020/0383799 A1 | 12/2020 | Cain |
| 2020/0390565 A1 | 12/2020 | Jimenez et al. |
| 2020/0397593 A1 | 12/2020 | Davenport et al. |
| 2020/0405497 A1 | 12/2020 | Olmos et al. |
| 2020/0405498 A1 | 12/2020 | Gray et al. |
| 2020/0405499 A1 | 12/2020 | Gerbec et al. |
| 2020/0405500 A1 | 12/2020 | Cain |
| 2021/0007860 A1 | 1/2021 | Glerum et al. |
| 2021/0015626 A1 | 1/2021 | Suddaby |

(56) References Cited

U.S. PATENT DOCUMENTS

| | | |
|---|---|---|
| 2021/0030555 A1 | 2/2021 | Weiman et al. |
| 2021/0030561 A1 | 2/2021 | Gleason |
| 2021/0045891 A1 | 2/2021 | Rogers et al. |
| 2021/0045892 A1 | 2/2021 | Rogers et al. |
| 2021/0052395 A1 | 2/2021 | Iott et al. |
| 2021/0068959 A1 | 3/2021 | McLuen et al. |
| 2021/0068974 A1 | 3/2021 | Cowan et al. |
| 2021/0068982 A1 | 3/2021 | Carnes et al. |
| 2021/0077271 A1 | 3/2021 | Sharabani |
| 2021/0077272 A1 | 3/2021 | Eisen et al. |
| 2021/0085479 A1 | 3/2021 | Weiman et al. |
| 2021/0093462 A1 | 4/2021 | Lucasiewicz et al. |
| 2021/0106434 A1 | 4/2021 | Alheidt et al. |
| 2021/0113349 A1 | 4/2021 | Weiman et al. |
| 2021/0121299 A1 | 4/2021 | Hyder |
| 2021/0121300 A1 | 4/2021 | Weiman et al. |
| 2021/0137697 A1 | 5/2021 | Weiman |
| 2021/0137699 A1 | 5/2021 | Jang et al. |
| 2021/0137701 A1 | 5/2021 | Miller et al. |
| 2021/0154811 A1 | 5/2021 | Spreiter et al. |
| 2021/0161678 A1 | 6/2021 | Dewey et al. |
| 2021/0177618 A1 | 6/2021 | Branch et al. |
| 2021/0186706 A1 | 6/2021 | Spitler et al. |
| 2021/0186709 A1 | 6/2021 | Weiman et al. |
| 2021/0196470 A1 | 7/2021 | Shoshtaev |
| 2021/0205092 A1 | 7/2021 | Glerum et al. |
| 2021/0205094 A1 | 7/2021 | Weiman et al. |
| 2021/0220145 A1 | 7/2021 | Stein |
| 2021/0220147 A1 | 7/2021 | Berry |
| 2021/0236298 A1 | 8/2021 | Weiman et al. |
| 2021/0251770 A1 | 8/2021 | Purcell et al. |
| 2021/0251776 A1 | 8/2021 | Daffinson et al. |
| 2021/0259848 A1 | 8/2021 | Kang et al. |
| 2021/0259849 A1 | 8/2021 | Robinson et al. |
| 2021/0259850 A1 | 8/2021 | Eisen et al. |
| 2021/0267767 A1 | 9/2021 | Stein |
| 2021/0275317 A1 | 9/2021 | Spetzger |
| 2021/0275318 A1 | 9/2021 | Reimels |
| 2021/0275319 A1 | 9/2021 | Reimels |
| 2021/0275321 A1 | 9/2021 | Seifert et al. |
| 2021/0282938 A1 | 9/2021 | Nichols et al. |
| 2021/0298915 A1 | 9/2021 | Faulhaber |
| 2021/0298916 A1 | 9/2021 | Melkent et al. |
| 2021/0307920 A1 | 10/2021 | Walker et al. |
| 2021/0315705 A1 | 10/2021 | Altarac et al. |
| 2021/0322179 A1 | 10/2021 | Miller et al. |
| 2021/0322181 A1 | 10/2021 | Predick |
| 2021/0322182 A1 | 10/2021 | Faulhaber |
| 2021/0330472 A1 | 10/2021 | Shoshtaev |
| 2021/0346174 A1 | 11/2021 | Flint et al. |
| 2022/0015924 A1 | 1/2022 | Freedman et al. |
| 2022/0047312 A1 | 2/2022 | Seykora et al. |
| 2022/0133336 A1 | 5/2022 | Tsai et al. |
| 2022/0133498 A1 | 5/2022 | Josse et al. |
| 2022/0133499 A1 | 5/2022 | Josse et al. |
| 2022/0387184 A1 | 12/2022 | Josse et al. |

FOREIGN PATENT DOCUMENTS

| | | |
|---|---|---|
| EP | 0 767 636 A1 | 4/1997 |
| EP | 0 880 950 A1 | 12/1998 |
| EP | 0 857 042 B1 | 11/2001 |
| EP | 1 442 732 A1 | 8/2004 |
| EP | 1 124 512 B1 | 9/2004 |
| EP | 1 107 711 B1 | 10/2004 |
| EP | 1 506 753 A1 | 2/2005 |
| EP | 1 459 711 B1 | 7/2007 |
| EP | 2954860 A2 | 12/2015 |
| EP | 3031424 A1 | 6/2016 |
| EP | 3 069 694 A1 | 9/2016 |
| EP | 3213720 A1 | 9/2017 |
| FR | 2781998 A1 | 2/2000 |
| FR | 3082115 A1 | 12/2019 |
| GB | 2 377 387 A | 1/2003 |
| KR | 102192022 B1 | 12/2020 |
| WO | 92/14423 A1 | 9/1992 |
| WO | 97/ 00054 A1 | 1/1997 |
| WO | 99/ 26562 A1 | 6/1999 |
| WO | 99/66867 A1 | 12/1999 |
| WO | 00/12033 A1 | 3/2000 |
| WO | 00/25706 A1 | 5/2000 |
| WO | 00/ 49977 A1 | 8/2000 |
| WO | 02/19952 A1 | 3/2002 |
| WO | 03/105673 A2 | 12/2003 |
| WO | 2006116850 A1 | 11/2006 |
| WO | 2012139022 A2 | 10/2012 |
| WO | 2014/133755 A1 | 9/2014 |
| WO | 2015063721 A1 | 5/2015 |
| WO | 2015198335 A1 | 12/2015 |
| WO | 2016057940 A1 | 4/2016 |
| WO | 2017/168208 A1 | 10/2017 |
| WO | 2018049227 A1 | 3/2018 |
| WO | 2021055323 A1 | 3/2021 |

OTHER PUBLICATIONS

International Search Report, and Written Opinion for Application. No. PCT/US2019/019067, dated Jun. 3, 2019.

International Search Report and Written Opinion for Application No. PCT/US2019/019060, dated Jun. 5, 2019.

International Search Report and Written Opinion, PCT/IB2020/000932, dated Jul. 29, 2021.

International Search Report and Written Opinion in Application No. PCT/US2022/016809 dated Jul. 27, 2022.

International Search Report and Written Opinion in Application No. PCT/US2022/027695 dated Jul. 27, 2022.

International Search Report and Written Opinion in Application No. PCT/US2022/027200 dated Aug. 19, 2022.

International Search Report and Written Opinion in Application No. PCT/US2022/016831 dated Sep. 29, 2022.

International Search Report and Written Opinion in Application No. PCT/US2022/030094 dated Sep. 16, 2022.

* cited by examiner

EXPANDABLE INTERBODY IMPLANT

CROSS-REFERENCE TO RELATED APPLICATIONS

This application incorporates by reference the entire contents of U.S. application Ser. No. 17/307,578, titled EXTERNALLY DRIVEN EXPANDABLE INTERBODY AND RELATED METHODS, and filed May 5, 2021.

FIELD

The present technology is generally related to an externally driven expandable interbody implant for use in a medical procedure related to the spine. In some embodiments, disclosed implants may be used in an anterior cervical discectomy and fusion (ACDF) procedure although other uses in other areas of the spine or between two bones are also contemplated.

BACKGROUND

Mechanically operated interbody implants may be used to align and/or realign a patient's spine during a medical procedure and/or for purposes of fusion, degenerative tissue and/or trauma/repair procedures. Conventional implants designed for the Thoracic and Lumbar region of the spine often include top and bottom endplates and a mechanical means to separate the top and bottom endplates. The mechanical mechanisms to separate the top and bottom endplates are often cumbersome and require a large footprint that is often unsuitable, for example, for ACDF type surgeries of the cervical portion of the spine.

SUMMARY

The techniques of this disclosure generally relate to an expandable interbody implant including a superior endplate and an inferior endplate hingedly coupled and which may further include a hinged coupling to a core, for example. The superior and inferior endplates may be moved and/or locked in a multitude of expanded and/or lordosed or kyphosed or otherwise angled configurations via a locking screw, for example.

In one aspect, the present disclosure provides for an expandable implant movable between a contracted position and an expanded position, for example. In various embodiments, the expandable body may extend from a proximal end to a distal end in a proximal-to-distal direction, extend from a first lateral side to a second lateral side in a widthwise direction, and extend from a superior end to an inferior end in a vertical direction, for example. In various embodiments, the expandable body may be defined, at least partly, by a superior endplate, an inferior endplate opposite the superior endplate, and a core disposed between the superior endplate and inferior endplate, for example. In various embodiments, the superior endplate may include a first screw engagement surface disposed on a proximal end of the superior endplate, for example. In various embodiments, the inferior endplate may include a second screw engagement surface disposed on a proximal end of the inferior endplate, for example. In various embodiments, the core may include a threaded screw aperture disposed on a proximal end of the core and extending in the proximal-to-distal direction, for example. In various embodiments, a pin may extend in the widthwise direction and be disposed through the superior endplate, the inferior endplate, and the core, for example. In various embodiments, the pin may hingedly couple the superior endplate and the inferior endplate, for example. In various embodiments, a threaded locking screw may be disposed in the threaded screw aperture and may be movable in the proximal-to-distal direction between a locked position and an unlocked position, for example. In at least some embodiments, in the locked position, the threaded locking screw engages the first screw engagement surface and the second screw engagement surface.

In another aspect, the disclosure provides for a method of expanding and locking an expandable implant. The method may include the step of providing an expandable implant movable between a contracted position and an expanded position, for example. In various embodiments, the expandable body may extend from a proximal end to a distal end in a proximal-to-distal direction, extend from a first lateral side to a second lateral side in a widthwise direction, and extend from a superior end to an inferior end in a vertical direction, for example. In various embodiments, the expandable body may be defined, at least partly, by a superior endplate, an inferior endplate opposite the superior endplate, and a core disposed between the superior endplate and inferior endplate, for example. In various embodiments, the superior endplate may include a first screw engagement surface disposed on a proximal end of the superior endplate, for example. In various embodiments, the inferior endplate may include a second screw engagement surface disposed on a proximal end of the inferior endplate, for example. In various embodiments, the core may include a threaded screw aperture disposed on a proximal end of the core and extending in the proximal-to-distal direction, for example. In various embodiments, a pin may extend in the widthwise direction and be disposed through the superior endplate, the inferior endplate, and the core, for example. In various embodiments, the pin may hingedly couple the superior endplate and the inferior endplate, for example. In various embodiments, a threaded locking screw may be disposed in the threaded screw aperture and may be movable in the proximal-to-distal direction between a locked position and an unlocked position, for example. In at least some embodiments, in the locked position, the threaded locking screw engages the first screw engagement surface and the second screw engagement surface. The method may further include the step of expanding the expandable implant via the first gripping indentation and the second gripping indentation, for example. The method may further include the step of locking the expandable implant by rotating the threaded locking screw such that it linearly translates from the proximal end towards the distal end thereby directly contacting the first screw engagement surface and the second screw engagement surface.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 12 is a reference drawing showing the human spine of which various disclosed implant embodiments may be installed in.

DETAILED DESCRIPTION

Figure 1:
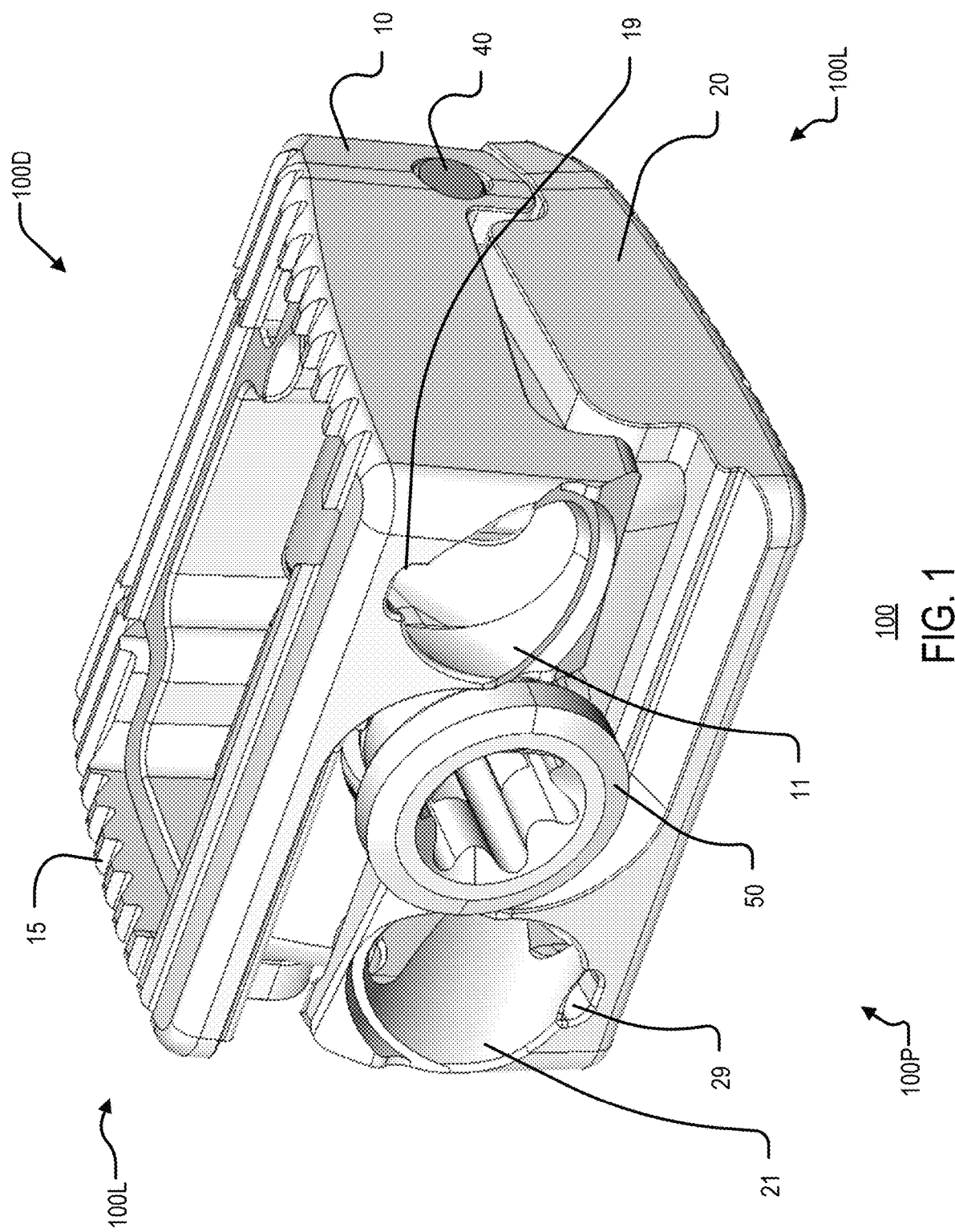
FIG. 1 is a perspective view of an expandable implant.

Embodiments of the present disclosure relate generally, for example, to spinal stabilization systems, and more particularly, to surgical instruments for use with spinal stabilization systems. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise.

Referring to FIGS. 1-11 generally, various spinal implants 100 are disclosed. The components of spinal implant 100 can be fabricated from biologically acceptable materials suitable for medical applications, including metals, synthetic polymers, ceramics and bone material and/or their composites. For example, the components of spinal implant 100, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Figure 12:
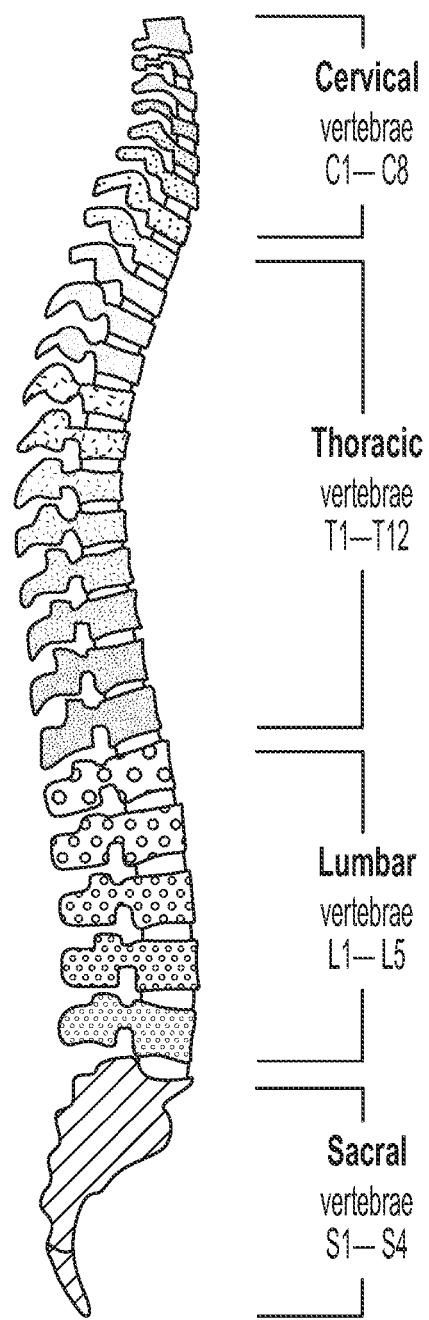
Figure 13:
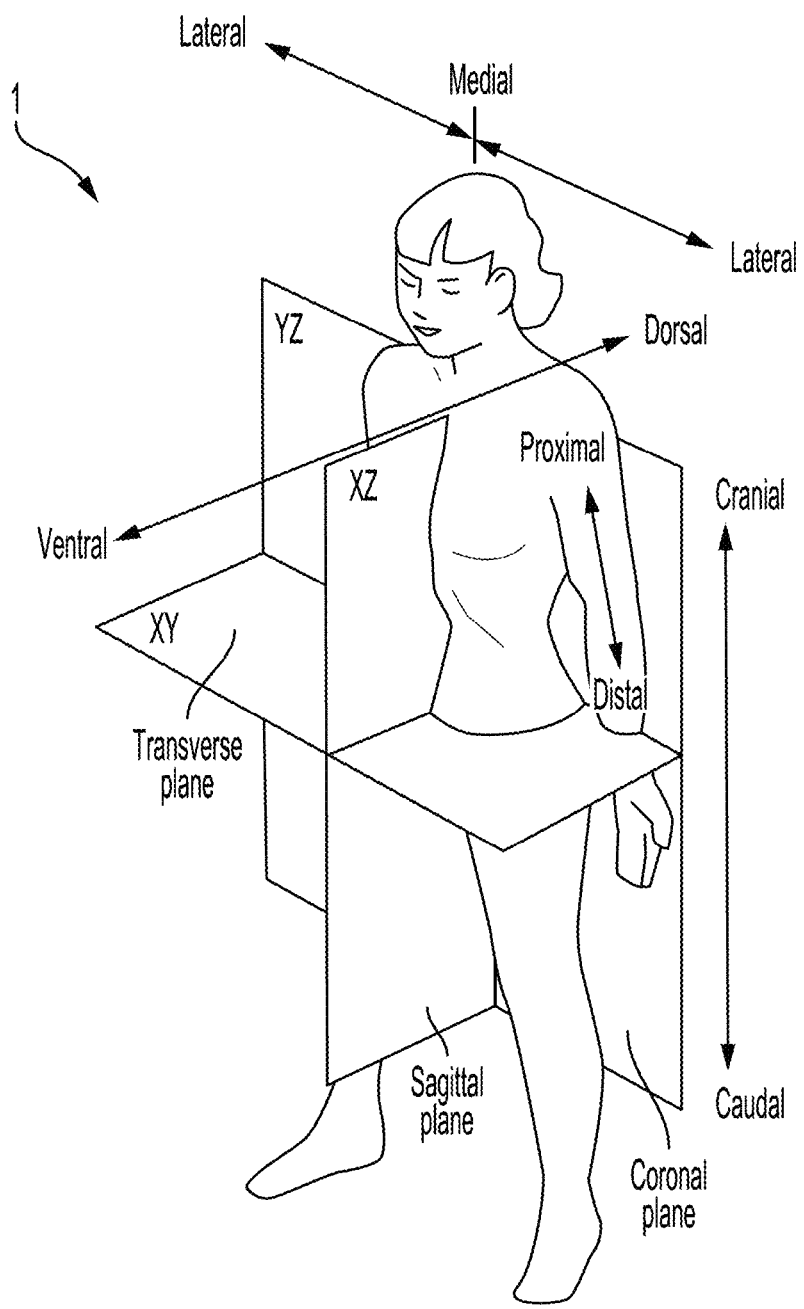
FIG. 13 is a reference drawing showing various planes and reference directions of which the various disclosed implant embodiments may move in or act in with respect to a patient.

Referring generally to FIGS. 1-11 various embodiments of an expandable implant 100 are disclosed. FIGS. 12-13 are reference drawings showing the human spine and various medical terminology as it relates to planes and directions of which various components of implant 100 may act or move in.

Figure 2:
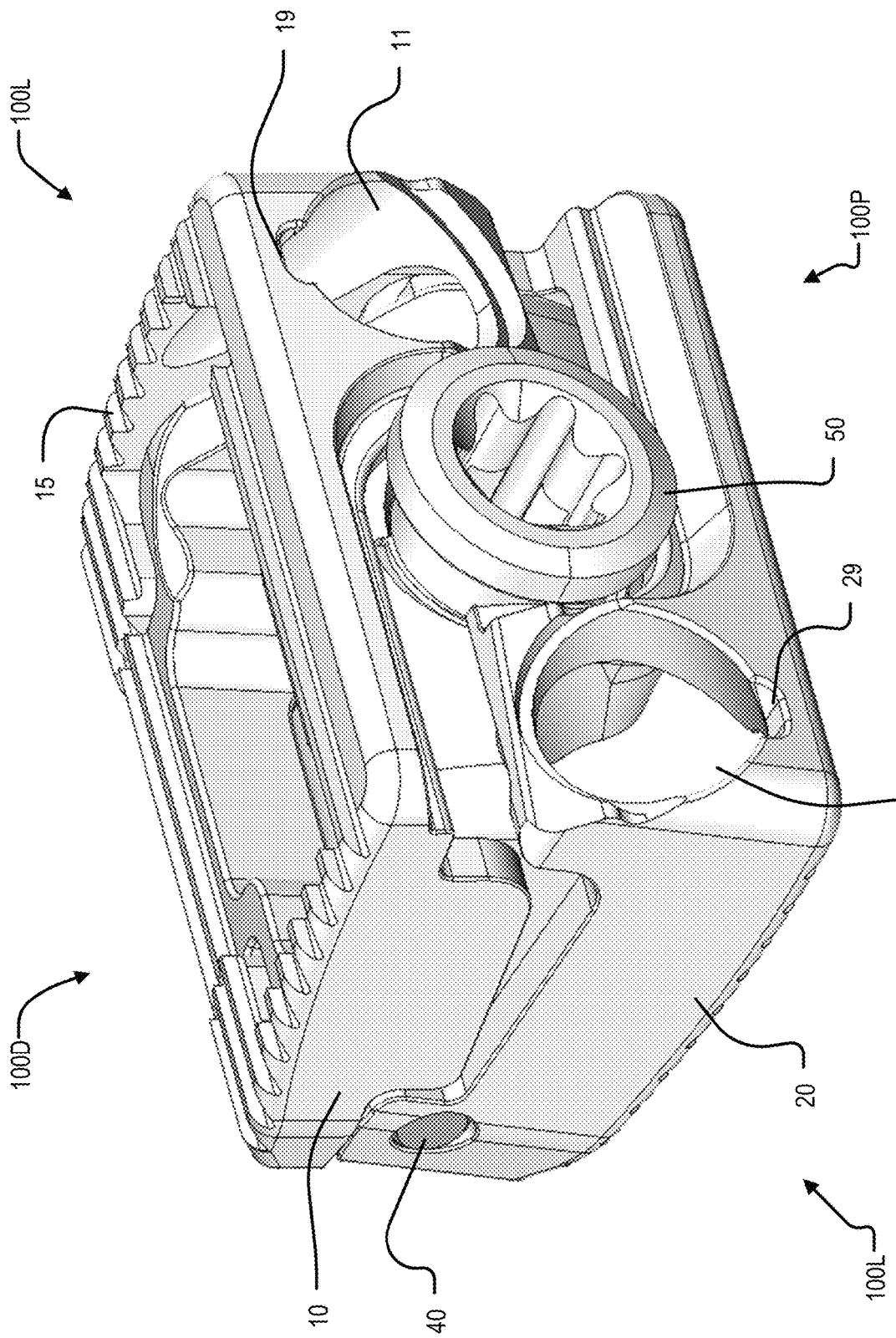
FIG. 2 is an alternate perspective view of an expandable implant.
Figure 3:
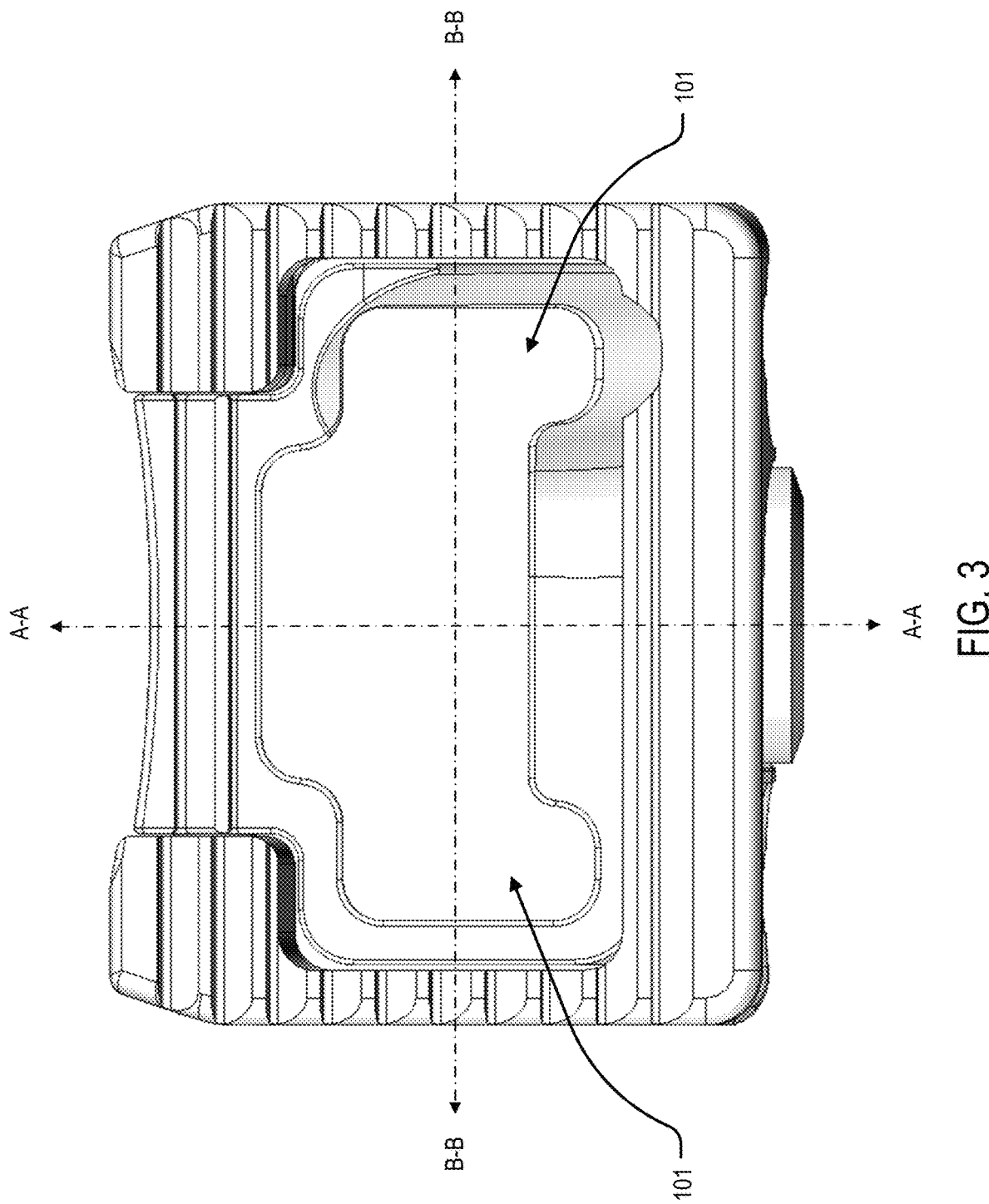
FIG. 3 is a top down view of an expandable implant.

FIGS. 1-2 illustrate example perspective views of an expandable implant 100 in a partially expanded position and FIG. 3 is a top down view of an expandable implant 100. As illustrated, expandable implant 100 may include a proximal end 100*p*, a distal end 100*d*, and first and second lateral sides 1001. The proximal end 100*p* may include a screw guide aperture 31 and a pair of gripping indentations 19, 29 on opposite sides of the screw guide aperture 31, for example. Additionally, a pair of bone screw apertures 11, 21 may be positioned on the proximal end 100*p*, for example. In various embodiments, and as illustrated in FIGS. 1-2, the gripping indentations 19, 29 may be formed as a cutout portion adjoining the bone screw apertures 11, 21, for example. Implant 100 may be referred to as an externally expandable implant because an end user such as a surgeon may use a surgical tool to open and close implant 100, for example an external tool may adjust the lordotic angle of implant 100. Once implant 100 is expanded to an appropriate lordotic angle (also referred to as angle of inclination), an end user may fix the relative angle of the superior endplate 10 relative to the inferior endplate 20 by tightening locking screw 50, for example. Various examples of surgical tools for expanding and contracting implant 100 as well as various examples of a surgical tool for tightening locking screw 50 are disclosed in FIGS. 24-35 and the corresponding discussion thereof of U.S. application Ser. No. 17/307,578, the entire contents of which are incorporated herein by reference in their entirety. At least one advantage of relying on an external tool to adjust a lordotic angle of implant 100 may be the reduction of internal components within implant 100 relative to other forms of implants relying on various moving mechanisms and/or expansion mechanisms, for example. Accordingly, in various embodiments, implant 100 may have a relatively large void space in the interior thereof, which may facilitate a fusion process during an ACDF procedure. For example, implant 100 may have a relatively large internal space for packing of bone growth promoting materials and/or bone grafts.

As illustrated in FIG. 3, implant 100 may extend in a proximal-to-distal direction from the proximal end 100*p* to the distal end 100*d* though axis A-A through the center of the implant 100, for example. Implant 100 may extend in a widthwise direction (also referred to as lateral direction) from the first lateral side 100l to the second lateral side 100l through axis B-B through the center of the implant 100, for example. The axis A-A may be perpendicular and/or substantially perpendicular to the axis B-B. For example, the proximal-to-distal direction may be perpendicular to the widthwise direction.

Figure 4:
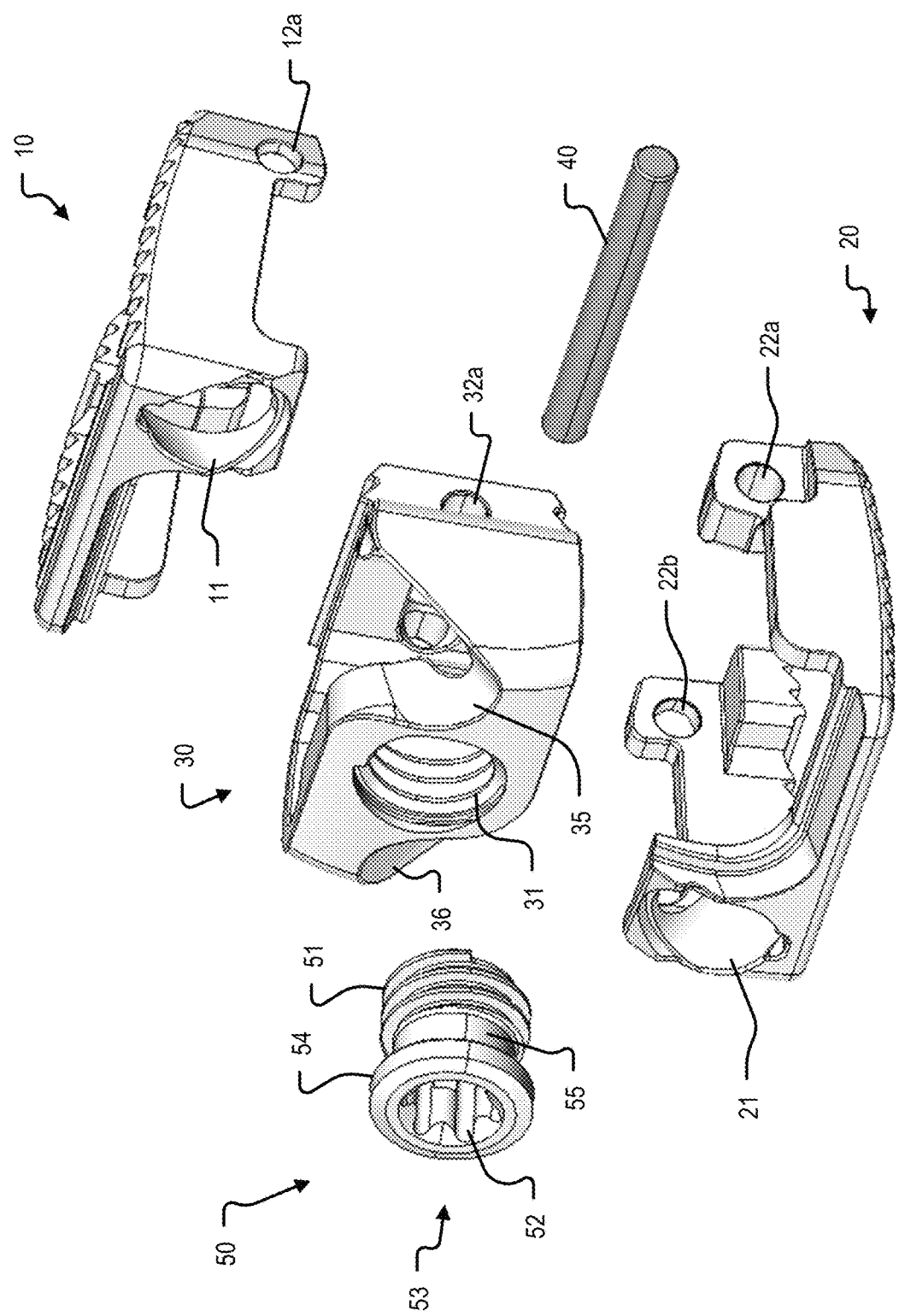
FIG. 4 is a perspective exploded parts view of an expandable implant.
Figure 5:
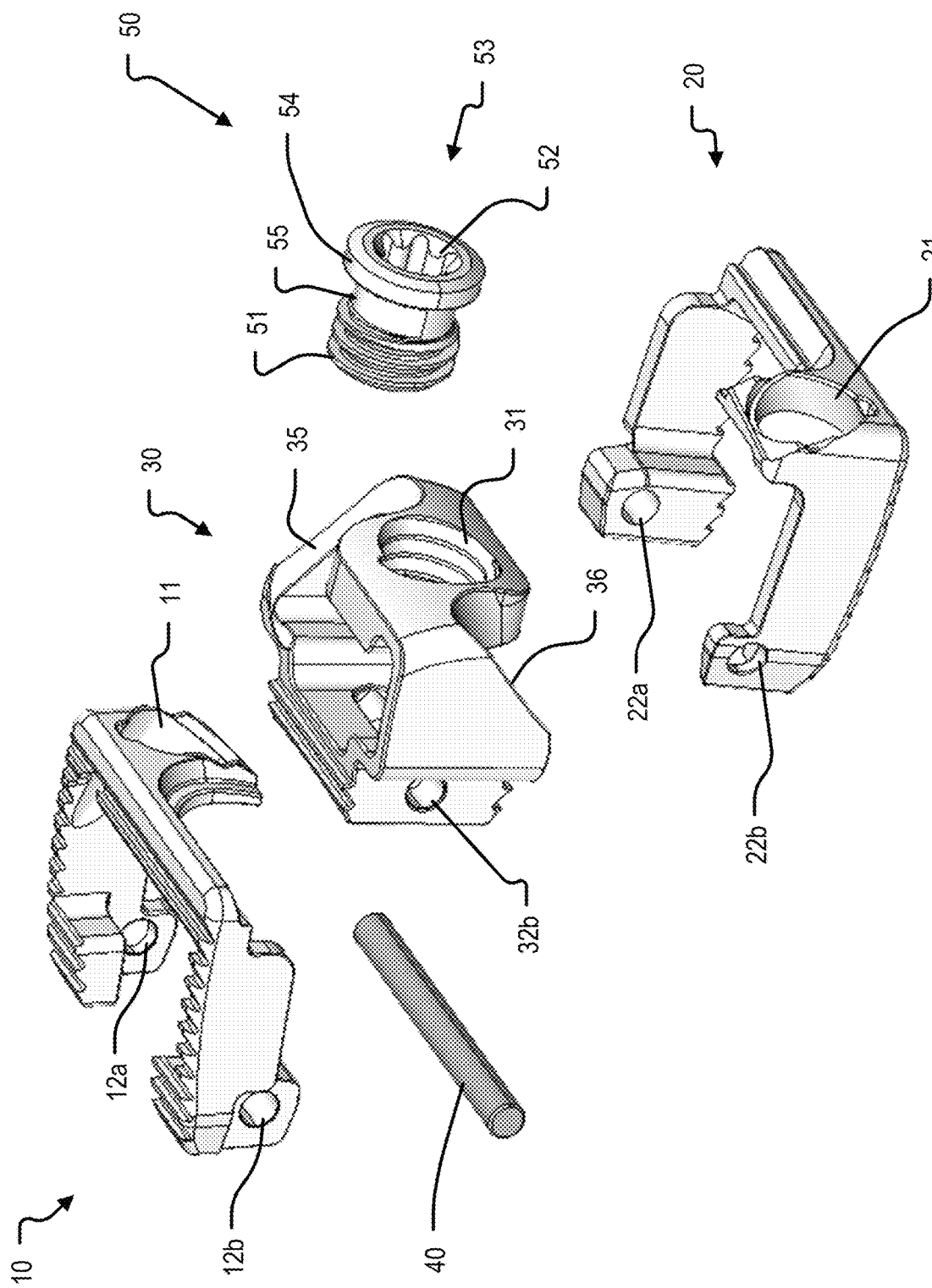
FIG. 5 is an alternate perspective exploded parts view of an expandable implant.

FIGS. 4-5 illustrate example exploded parts views of an expandable implant 100. Implant 100 may include a superior endplate 10 and an inferior endplate 20 defining the top and bottom surfaces of implant 100, for example. The superior endplate and inferior endplate 10, 20 may be hingedly coupled to one another via pin 40, for example. The superior and inferior endplates 10, 20 may be adjustable with respect to one another in the vertical direction and inclinable with respect to one another, i.e., capable of distraction and lordosis by rotation around pin 40, for example. Additionally, a core 30 may be disposed centrally within implant 100 and the superior endplate 10 and inferior endplate 20 may be hingedly coupled to the core 30 via pin 40, for example. Pin 40 may extend in the lateral direction through pin receiving apertures 12a, 12b of superior endplate 10, pin receiving apertures 32a, 32b of core 30, and pin receiving apertures 22a, 22b of inferior endplate 20, for example. In some embodiments, pin 40 may be referred to as a rod or a dowel, for example. Additionally, in some embodiments, the superior endplate 10, inferior endplate 20, and core 30 may collectively be referred together as an expandable body.

In some embodiments, pin 40 may be "press fit" to core 30 by extending through pin receiving apertures 32a, 32b (may also be referred to as an interference fit). As used herein, the terms "press fit" and "interference fit" are intended to have their ordinary technical meaning, for example a form of fastening between two tight fitting mating parts that produces a joint which is held together by friction after the parts are pushed together. In some embodiments, the connection of pin 40 to core 30 may be a press fit or interference fit where the components are tightly held together such that the core 30 may not rotate relative to pin 40 and/or pin 40 may be fixed in position relative to core 30, for example. At least one advantage of utilizing a press fit connection may be that the connection assures rigid, permanent support for pin 40 at each tension point defined by pin receiving apertures 32a, 32b with no relative movement thereby reducing wear and/or fatigue while providing a shaft and/or pivot point for superior endplate 10 and inferior endplate 20 to rotate about. However, in other embodiments, some rotation may be possible.

In various embodiments, pin 40 may be "slip fit" to superior endplate 10 by extending through pin receiving apertures 12a, 12b, for example. Similarly, in various embodiments pin 40 may be "slip fit" to inferior endplate 20 by extending through pin receiving apertures 22a, 22b, for example. As used herein, the term "slip fit" is intended to have an ordinary technical meaning, for example, a form of fastening between two relatively loose but snug mating parts that produces a joint which allows rotation and/or movement.

The proximal end 100p of superior endplate 10 may include a first bone screw aperture 11 extending through the upper surface of superior endplate 10 for engaging with a superior vertebra, for example. In the example embodiment, the first bone screw aperture 11 extends from the proximal end 100p of superior endplate 10 through a bone graft aperture 101 of superior endplate 10 (see FIG. 3). Additionally, core 30 may include a first bone screw cutout 35 comprising an arcuate channel for accommodating a bone screw extending through the first bone screw aperture 11, for example.

Similarly, the proximal side 100p of inferior endplate 20 may include a second bone screw aperture 21 extending through the lower surface of inferior endplate 20 for engaging with an inferior vertebra, for example. In the example embodiment, the second bone screw aperture 21 extends from the proximal end 100p of inferior endplate 20 through a bone graft aperture 101 of inferior endplate 20 (see FIG. 3). Additionally, in various embodiments, each of superior endplate 10 and inferior endplate 20 may include a bone graft aperture 101 having substantially the same size and shape, for example. Additionally, core 30 may include a second bone screw cutout 36 comprising an arcuate channel for accommodating a bone screw extending through the second bone screw aperture 21, for example.

In various embodiments, core 30 may include a screw guide aperture 31 (also referred to as a locking screw guide aperture). Screw guide aperture 31 may be disposed in a central position of implant 100 at proximal end 100p, for example. Screw guide aperture 31 may include a female thread pattern having a size and shape corresponding to a male thread pattern 51 of locking screw 50, for example. Screw guide aperture 31 may rotatably support a locking screw 50 therein such that rotation of locking screw 50 may cause linear translation of locking screw 50 in the proximal-to-distal direction along axis A-A, for example.

In various embodiments, locking screw 50 may have an outside circumferential surface including a male thread pattern 51 at a distal end thereof, for example. Locking screw 50 may be disposed in screw guide aperture 31 and move forward and backward in the proximal/distal directions upon rotation of the locking screw 50. For example, locking screw 50 may include an internal circumferential surface 52 having any suitable size and shape for engaging with a driver to rotate locking screw 50. For example, a hexolobular shape, a torx shape, a hex shape, polygonal shape, etc. In various embodiments, the locking screw 50 may include a central aperture 53 extending therethrough; although, in some embodiments a distal end of locking screw 50 may be closed and the proximal side of locking screw 50 may still have a central aperture 53 extending partially through locking screw 50. In at least one embodiment, a distal end of locking screw 50 is closed and an outside distal surface of locking screw 50 may have a hemispherical and/or cup like shape that is indented or outdented for applying a compressive force at a point location. In other embodiments, a distal surface of locking screw 50 may be substantially flat and/or planar for applying a relatively more distributed compressive force. In the example embodiment, locking screw 50 may include a head portion 54, comprising an annular ring that extends out laterally farther than the maximum diameter of the threads of thread pattern 51, for example. For example, a diameter of head portion 54 may be larger than a maximum diameter of thread pattern 51, for example. However, in other embodiments, a diameter of head portion 54 may be about the same and/or substantially the same as a maximum diameter of thread pattern 51. In the example embodiment, locking screw 50 may include a smooth shaft portion 55 disposed central to and between thread pattern 51 and head portion 54, for example. This may allow the locking screw 50 to move forward and backward within screw guide aperture 31 a distance before a distal surface of head portion 54 engages with corresponding surfaces of the superior and inferior endplates 10, 20, as will be explained in further detail below.

In various embodiments, locking screw 50 may fix a relative angle of inclination between the superior and inferior endplates 10, 20 (a lordotic angle). For example, locking screw 50 may be rotated such that it linearly translates and/or moves from a proximal end 100p towards the distal end 100d thereby urging various contact surfaces of the superior endplate 10, core 30, and inferior endplate 20 into frictional engagement. For example still, locking screw 50 may apply a compressive force frictionally engaging the superior endplate 10, core 30, and inferior endplate 20 such that they are locked in a relative position to one another, as will be explained in further detail below.

Figure 6:
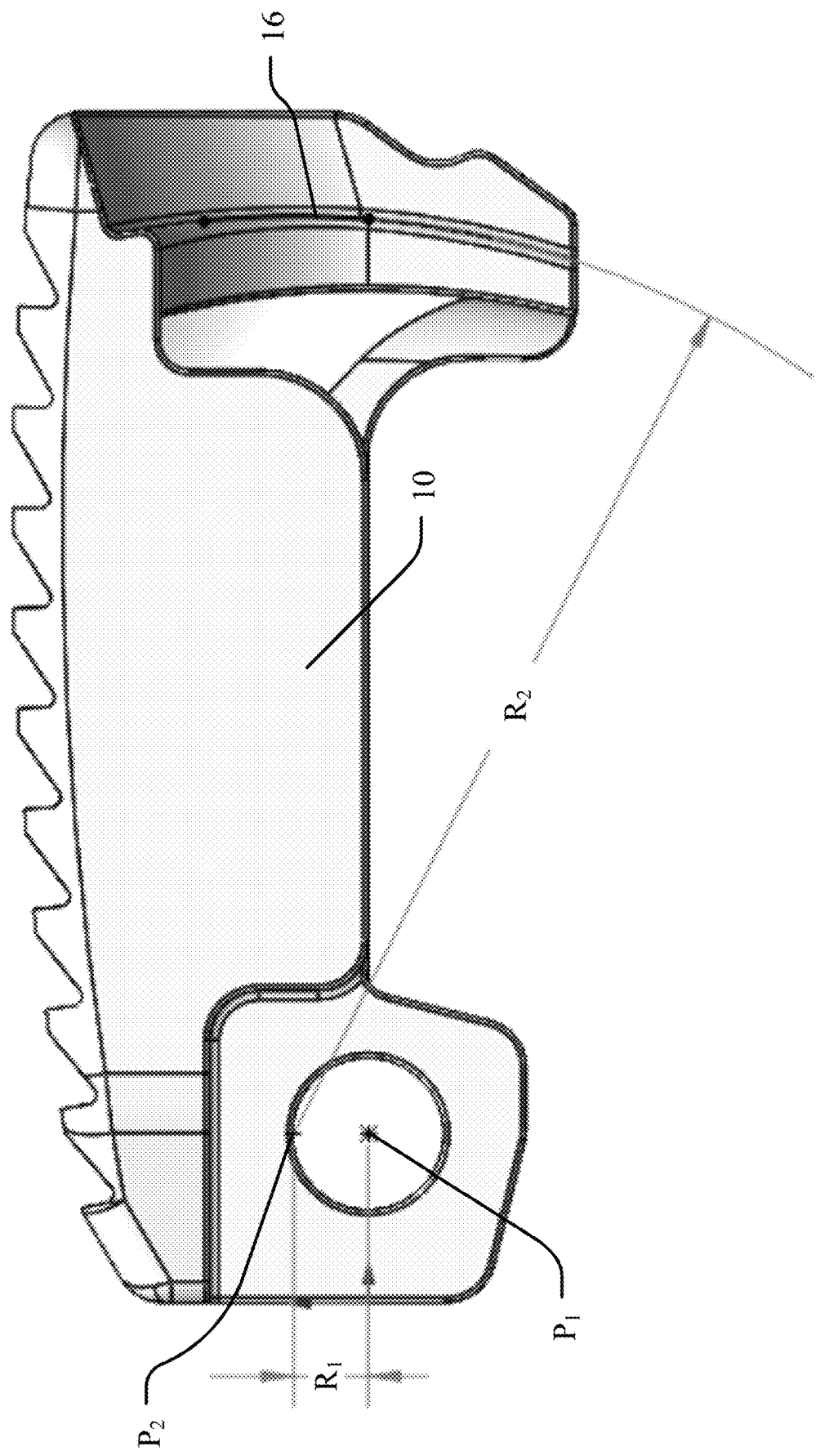
FIG. 6 is a side view of a superior endplate.

FIG. 6 illustrates a side view of superior endplate 10. In the example embodiment, and as explained above, superior endplate 10 may include a pair of pin receiving apertures 12a, 12b. In the side view of FIG. 6, only pin receiving aperture 12b is labeled. In various embodiments, pin receiving apertures 12a, 12b may be coaxially aligned circular apertures having the same radius, for example. As illustrated, pin receiving aperture 12b may comprise a circle having a radius $R_1$ and a center point $P_1$ defining a center of pin receiving apertures 12a, 12b and/or an axis of rotation that superior endplate 10 may rotate and/or pivot with respect to. For example, superior endplate 10 may be hingedly coupled to pin 40 and rotatable about an axis of rotation defined by center point $P_1$, for example. Additionally, in the example embodiment, superior endplate 10 may include an engagement surface 16 (see also FIG. 10). In various embodiments, engagement surface 16 may be a curved surface defined (in part or in total) by a segment of a circle having a radius $R_2$. In various embodiments, a center point $P_2$ of a circle defining the curved engagement surface 16 may be offset from center point $P_1$, for example. In the example embodiment, center point $P_2$ is vertically above center point $P_1$ by a distance approximating radius $R_1$. However, in other embodiments, center point $P_2$ may be offset by a greater amount or even a lesser amount than illustrated. In various embodiments, $R_1$ may be about 0.5 mm to about 1 mm and $R_2$ may be about 7 mm to about 12 mm. In at least one embodiment $R_1$ is about 0.75 mm and $R_2$ is about 9.25 mm. In various embodiments, the inferior endplate 20 may also have a similar geometrical relationship.

Consistent with the disclosure herein, a geometrical relationship between the offset center points $P_1$ and $P_2$ may have several advantages in terms of operability and functionality. At least one advantage is that the superior endplate 10 may have a natural tendency to apply a force against the head portion 54 of locking screw 50 such that locking screw 50 may function similar to a wedge preventing implant 100 from fully collapsing. For example, in various embodiments, a superior vertebrae and an inferior vertebrae may apply a closing force against implant 100 and the offset radii arrangement as explained above may facilitate the engagement surface 16 naturally contacting head portion 54 of locking screw 50. For example still, an end user such as a surgeon may expand implant 100 and the offset arrangement explained above may facilitate the function of keeping implant 100 lordosed at the chosen angle.

Figure 7:
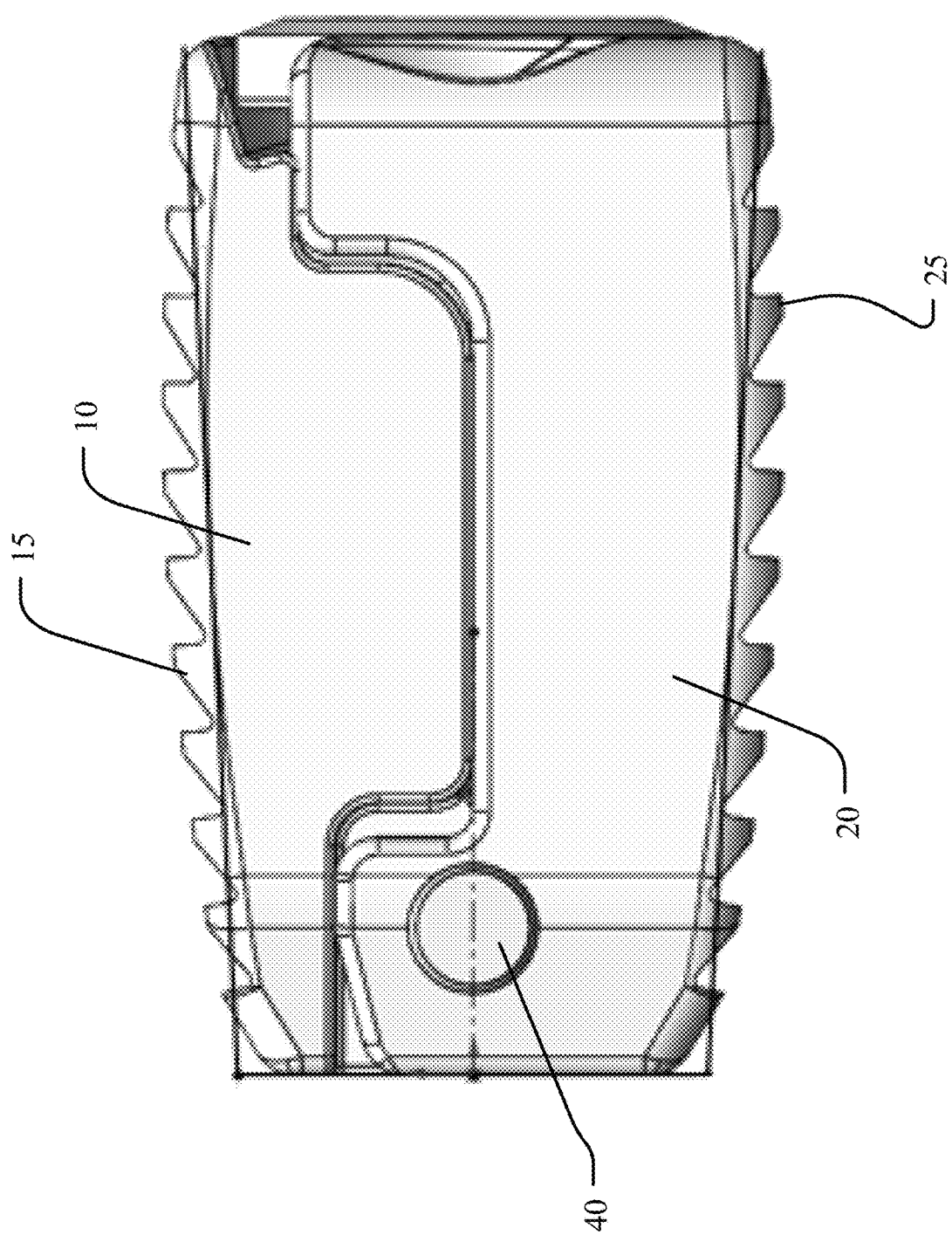
FIG. 7 is a side view of an expandable implant in a contracted position.
Figure 8:
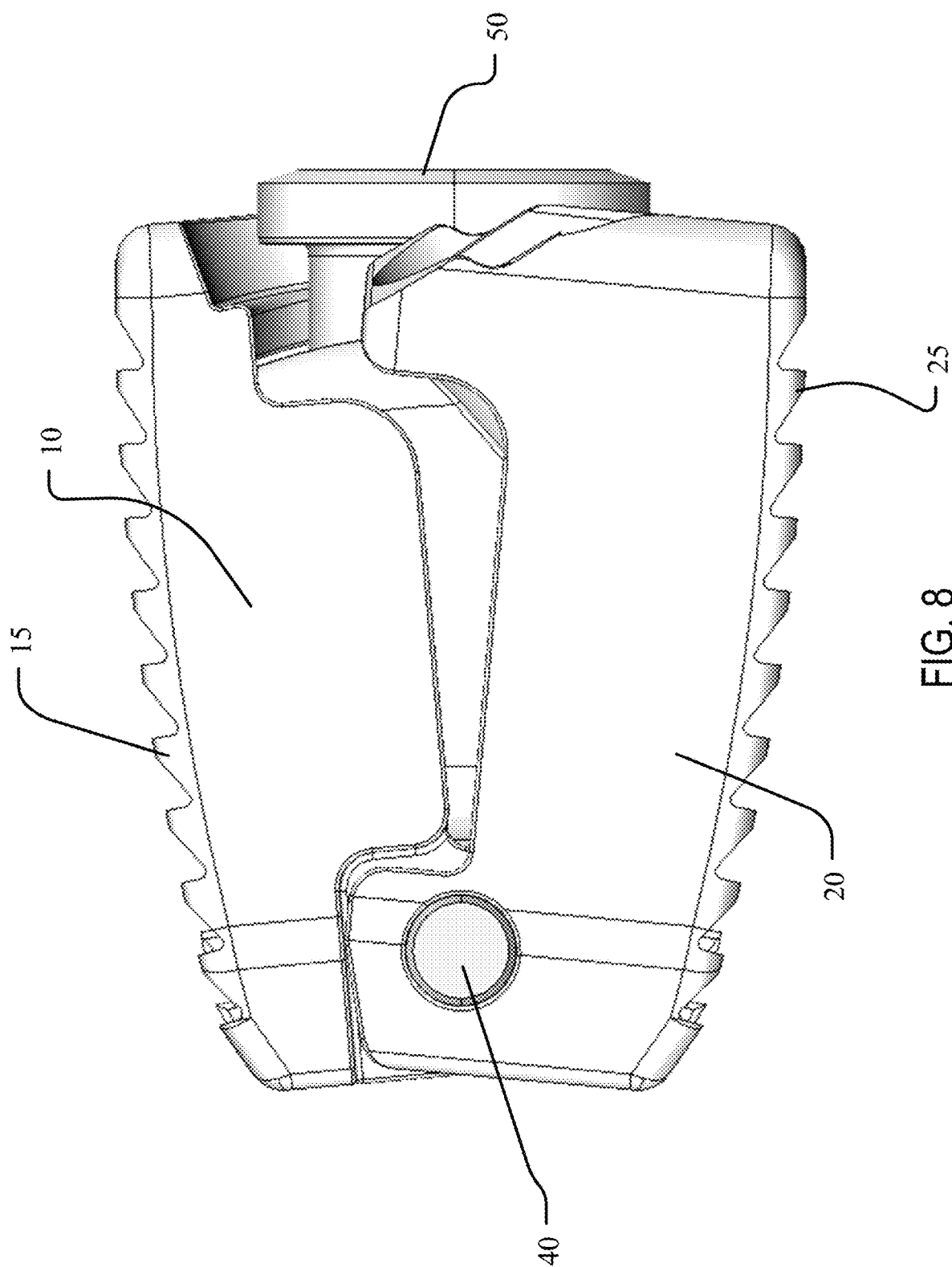
FIG. 8 is a side view of an expandable implant in an expanded position.

FIG. 7 is a side view of implant 100 in a collapsed position. In the illustrated embodiment, it is shown that superior endplate 10 includes a plurality of engagement features 15 and the inferior endplate 20 includes a plurality of engagement features 25. In the example embodiment, engagement features 15, 25 may comprise teeth or ridges extending in a lateral direction across the exposed surfaces of implant 100, for example. FIG. 8 is a side view of implant 100 in an expanded position. In the expanded position, it is shown that superior endplate 10 and inferior endplate 20 are inclined with respect to one another while core 30 retains locking screw 50 therein. In the expanded position, the superior endplate 10 may have pivoted about pin 40 upwards in the vertical direction and the inferior endplate 20 may have pivoted about pin 40 downwards in the vertical direction such that implant 100 is lordosed.

Figure 9:
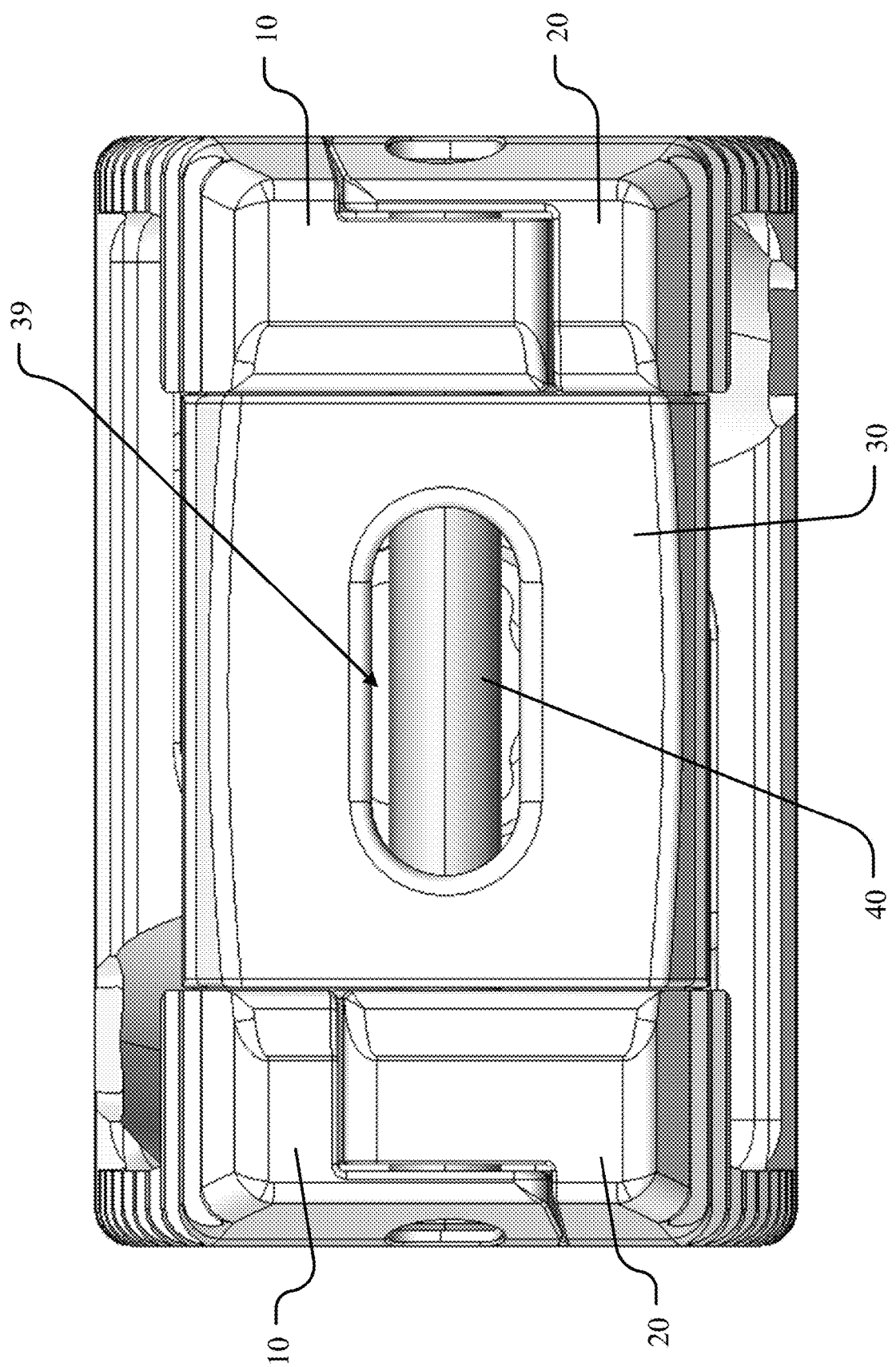
FIG. 9 is a rear view of an expandable implant.

FIG. 9 is a rear view of implant 100. In the example embodiment, it is shown that pin 40 extends through a slotted aperture 39 of core 30. In the example embodiment, slotted aperture 39 may extend in a lateral direction on a distal surface of core 30 and include curved ends at opposite lateral sides thereof. Additionally, a void space is shown surrounding pin 40 which may facilitate boney ingrowth during a fusion process, for example. FIG. 9 also illustrates that the superior endplate 10 and inferior endplate 20 are pivotally mated together.

Figure 10:
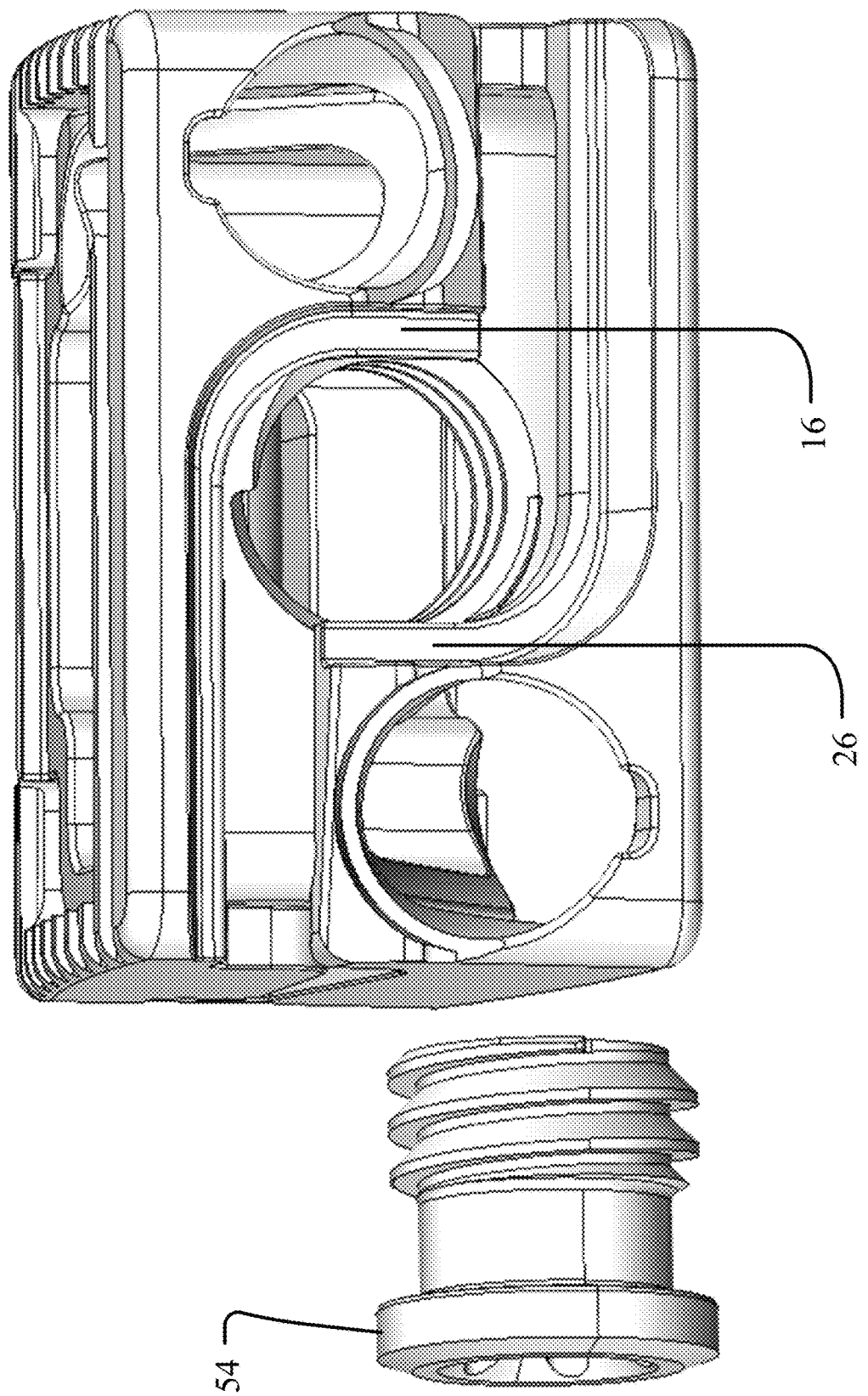
FIG. 10 is a front view of an expandable implant with a locking screw.

FIG. 10 illustrates a front view of implant 100 and a side view of locking screw 50. In the example illustration, it is shown that a backside (distal side) of head portion 54 may contact screw engagement surface 16 of superior endplate 10 and screw engagement surface 26 of inferior endplate 20. Screw engagement surfaces 16, 26 may comprise curved indentations having a profile that corresponds to a radius of curvature of head portion 54. For example, screw engagement surfaces 16, 26 may be shaped in a similar way to one another and locking screw 50 to contact the backside (distal side) of head portion 54 of locking screw 50 while also having enough clearance laterally for locking screw 50 to rotate. In the example embodiment, when locking screw 50 is sufficiently tightened the backside (distal side) of head portion 54 may push against screw engagement surfaces 16, 26 causing various internal surfaces of superior endplate 10 and inferior endplate 20 to frictionally engage and/or bind together as will be explained with reference to FIG. 11 below.

Figure 11:
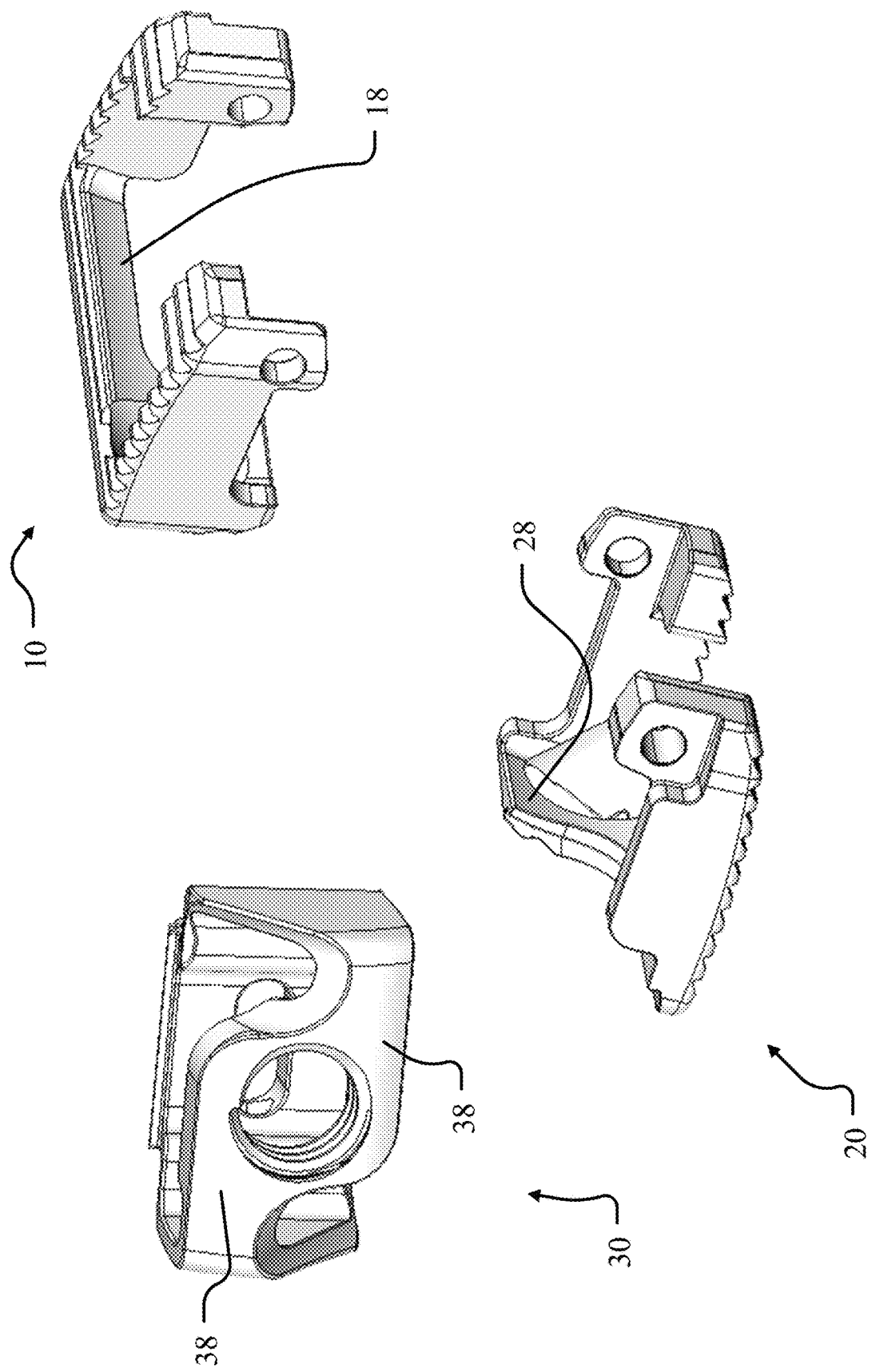
FIG. 11 is an exploded parts view of a superior endplate, inferior endplate, and core partially rotated for viewing of various engagement surfaces.

FIG. 11 is an exploded parts view with the superior endplate 10, inferior endplate 20, and core 30 rotated to illustrate the various surfaces that frictionally engage and/or bind together in a locked position. For example, superior endplate 10 may include a first binding surface 18 that may engage with and/or frictionally bind with a corresponding portion of binding surface 38 of core 30. First binding surface 18 may extend laterally on an upper interior surface of superior endplate 10, for example. Similarly, inferior endplate 20 may include a second binding surface 28 that may bind with and/or frictionally engage with a corresponding portion of binding surface 38 of core 30. In various embodiments, binding surfaces may be referred to as high friction surfaces, and/or engagement surfaces. In various embodiments, binding surface 38 of core 30 may face a proximal direction, and binding surfaces 18 and 28 may face a distal direction. In at least one embodiment, binding surfaces 18, 28, 38 comprise a high friction, roughened, and/or textured surface to facilitate jamming. In various embodiments, binding surfaces 18, 28, 38 may be surface roughened by a grit blast process. For example, an abrasive grit blasting process such as a sandblasting process including a surface treatment process to roughen the corresponding treated surfaces.

Accordingly, when locking screw 50 is sufficiently tightened the head portion 54 may push against screw engagement surfaces 16, 26 of superior endplate 10 and inferior endplate 20, respectively, thereby urging binding surfaces 18, 28, and 38 into a high friction and direct contact arrangement. In various embodiments, this high friction arrangement is sufficient to withstand a closing compressive force between a superior vertebra and an inferior vertebra. Additionally, locking screw 50 may function as a wedge between the curved engagement surfaces 16, 26 further preventing the collapse of implant 100. As explained herein, embodiments in accordance with the principles of this disclosure provide a highly adjustable implant 100 having an optimized and/or increased interior void space to facilitate a fusion process. In various example embodiments, implant 100 may be formed solely of five components, superior endplate 10, inferior endplate 20, core 30, pin 40, and locking screw 50. However, other embodiments may have more or less components and the aforementioned listing of components is not necessarily a precise and/or required listing.

In operation, a surgeon may expand implant 100 using an expansion tool. For example, an expansion tool having corresponding end portions that engage with gripping indentations 19, 29 and force open implant 100. Thereafter, and before fully tightening locking screw 50, implant 100 may naturally be biased towards a collapsed position as explained above yet may be prevented from collapsing due to engagement surfaces 16 and 26 and locking screw 50. For example, at least one of engagement surfaces 16, 26 may comprise a curved surface defined by a segment of a circle having a center point that is offset with respect to a center point and/or axis of extension of pin 40. Thereafter, an end user may tighten locking screw 50 such that locking screw 50 applies a compressive force against engagement surfaces 16 and 26 thereby pushing the superior endplate 10 and inferior endplate 20 against core 30. For example, locking screw 50 may apply a compressive force pushing the binding surfaces 18, 28 into a high friction engagement relationship with binding surface 38. As used herein, the term compressive force does not necessarily require that mechanical deflection occur but rather that two objects are pushed into direct contact by an applied force.

FIG. 12 is a reference drawing showing the human spine of which various disclosed implant embodiments may be installed in. FIG. 13 is a reference drawing showing various planes and reference directions of which the various disclosed implant embodiments may move in or act in with reference to a patient 1.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof

What is claimed is:

1. An expandable implant movable between a contracted position and an expanded position, comprising:
    an expandable body extending from a proximal end to a distal end in a proximal-to-distal direction, extending from a first lateral side to a second lateral side in a widthwise direction, and extending from a superior end to an inferior end in a vertical direction, the expandable body being defined by a superior endplate, an inferior endplate opposite the superior endplate, and a core disposed between the superior endplate and inferior endplate;
    wherein: the superior endplate comprises a first screw engagement surface disposed on a proximal end of the superior endplate; the inferior endplate comprises a second screw engagement surface disposed on a proximal end of the inferior endplate; and the core comprises a threaded screw aperture disposed on a proximal end of the core and extending in the proximal-to-distal direction;
    a pin extending in the widthwise direction and disposed through the superior endplate, the inferior endplate, and the core, the pin hingedly coupling the superior endplate and the inferior endplate; and
    a threaded locking screw disposed in the threaded screw aperture and movable in the proximal-to-distal direction between a locked position and an unlocked position, wherein, in the locked position, the threaded locking screw engages the first screw engagement surface and the second screw engagement surface.

2. The expandable implant of claim 1, wherein: the superior endplate further comprises a first gripping indentation disposed on the proximal end of the superior endplate; the inferior endplate further comprises a second gripping indentation disposed on the proximal end of the inferior endplate, and in the locked position, the threaded locking screw directly contacts the first screw engagement surface and the second screw engagement surface thereby fixing a relative position of the superior endplate and inferior endplate with respect to the core.

3. The expandable implant of claim 1, wherein: the superior endplate further comprises a first bone screw aperture disposed on the proximal end of the superior endplate; and the inferior endplate further comprises a second bone screw aperture disposed on the proximal end of the inferior endplate.

4. The expandable implant of claim 1, wherein: the superior endplate further comprises a first gripping indentation and a first bone screw aperture disposed on the proximal end of the superior endplate; the inferior endplate further comprises a second gripping indentation and a second bone screw aperture disposed on the proximal end of the inferior endplate; the first gripping indentation is disposed adjacent to and adjoins the first bone screw aperture; and the second gripping indentation is disposed adjacent to and adjoins the second bone screw aperture.

5. The expandable implant of claim 1, wherein: the superior endplate further comprises a first pin aperture and a second pin aperture disposed opposite the first pin aperture; the inferior endplate further comprises a third pin aperture and a fourth pin aperture disposed opposite the third pin aperture; the core further comprises a fifth pin aperture and a sixth pin aperture disposed opposite the third pin aperture; and the pin extends through the first, second, third, fourth, fifth, and sixth pin apertures.

6. The expandable implant of claim 5, wherein a first connection where the pin extends through the fifth pin aperture and sixth pin aperture comprises a press fit connection.

7. The expandable implant of claim 6, wherein:
a second connection where the pin extends through the first pin aperture and second pin aperture comprises a slip fit connection; and
a third connection where the pin extends through the third pin aperture and fourth pin aperture comprises a slip fit connection.

8. The expandable implant of claim 1, wherein the superior endplate and inferior endplate are hingedly connected to the core via the pin at the distal end of the expandable body.

9. The expandable implant of claim 8, wherein the core is fixedly coupled to the pin.

10. The expandable implant of claim 1, wherein the implant is expandable via a first gripping indentation disposed on the proximal end of the superior endplate and a second gripping indentation disposed on the proximal end of the inferior endplate.

11. The expandable implant of claim 1, wherein: the superior endplate further comprises a first pin aperture and a second pin aperture disposed opposite the first pin aperture; the inferior endplate further comprises a third pin aperture and a fourth pin aperture disposed opposite the third pin aperture; the core further comprises a fifth pin aperture and a sixth pin aperture disposed opposite the third pin aperture; the pin extends through the first, second, third, fourth, fifth, and sixth pin apertures; the first pin aperture comprises a circular shape having a first center point; the first screw engagement surface comprises a curved surface defined by a segment of a circle having a second center point; and the second center point is vertically disposed above the first center point.

12. The expandable implant of claim 1, wherein:
the first screw engagement surface comprises a first curved surface; and
the second screw engagement surface comprises a second curved surface.

13. The expandable implant of claim 12, wherein: the superior endplate further comprises a first binding surface disposed on an interior surface thereof and facing the distal end of the expandable body; the core further comprises a second binding surface disposed on an exterior surface thereof and facing the proximal end of the expandable body; and in the locked position, the first binding surface frictionally engages with the second binding surface.

14. The expandable implant of claim 12, wherein: the inferior endplate further comprises a third binding surface disposed on an interior surface thereof and facing the distal end of the expandable body; the core further comprises a second binding surface disposed on an exterior surface thereof and facing the proximal end of the expandable body; and in the locked position, the third binding surface frictionally engages with the second binding surface.

15. The expandable implant of claim 1, wherein: the superior endplate further comprises a first binding surface disposed on an interior surface thereof and facing the distal end of the expandable body; the core further comprises a second binding surface disposed on an exterior surface thereof and facing the proximal end of the expandable body; the inferior endplate further comprises a third binding surface disposed on an interior surface thereof and facing the distal end of the expandable body; and in the locked position, the locking screw urges the first binding surface against the second binding surface and urges the third binding surface against the second binding surface.

16. The expandable implant of claim 15, wherein the first binding surface, the second binding surface, and the third binding surface each comprise a high friction surface.

17. A method for expanding an implant, comprising:
providing an expandable implant having an expandable body extending from a proximal end to a distal end in a proximal-to-distal direction, extending from a first lateral side to a second lateral side in a widthwise direction, and extending from a superior end to an inferior end in a vertical direction, the expandable body being defined by a superior endplate, an inferior endplate opposite the superior endplate, and a core disposed between the superior endplate and inferior endplate;
wherein: the superior endplate comprises a first screw engagement surface disposed on a proximal end of the superior endplate; the inferior endplate comprises a second screw engagement surface disposed on a proximal end of the inferior endplate; and the core comprises a threaded screw aperture disposed on a proximal end of the core and extending in the proximal-to-distal direction;
a pin extending in the widthwise direction and disposed through the superior endplate, the inferior endplate, and the core, the pin hingedly coupling the superior endplate and the inferior endplate; and
a threaded locking screw disposed in the threaded screw aperture and movable in the proximal-to-distal direction between a locked position and an unlocked position expanding the expandable implant via the first gripping indentation and the second gripping indentation; and
locking the expandable implant by rotating the threaded locking screw such that it linearly translates from the proximal end towards the distal end thereby directly contacting the first screw engagement surface and the second screw engagement surface.

18. The method of claim 17, wherein: the superior endplate further comprises a first binding surface disposed on an interior surface thereof and facing the distal end of the expandable body; the core further comprises a second binding surface disposed on an exterior surface thereof and facing the proximal end of the expandable body; the inferior endplate further comprises a third binding surface disposed on an interior surface thereof and facing the distal end of the expandable body; and the locking the expandable implant step further comprises urging, by the locking screw, the first binding surface against the second binding surface and the third binding surface against the second binding surface.

19. The method of claim 17, wherein the expanding the expandable implant step further comprises hingedly rotating the superior endplate and inferior endplate about the pin.

20. The method of claim 19, wherein the expanding the expandable implant step further comprises hingedly rotating the superior endplate and inferior endplate about the pin while the core remains fixedly coupled to the pin.

* * * * *